(12) United States Patent
Green et al.

(10) Patent No.: US 8,349,583 B2
(45) Date of Patent: Jan. 8, 2013

(54) DISTINGUISHING CELLS IN A SAMPLE BY INACTIVATING EXTRACELLULAR ENZYME BEFORE RELEASING INTRACELLULAR ENZYME

(75) Inventors: Marc Green, Salisbury (GB); Robert Eisenthal, Bath (GB); Janet Eisenthal, legal representative, Bath (GB)

(73) Assignee: 3M Innovative Properties Company, St. Paul, MN (US)

( * ) Notice: Subject to any disclaimer, the term of this patent is extended or adjusted under 35 U.S.C. 154(b) by 262 days.

(21) Appl. No.: 11/919,832

(22) PCT Filed: May 3, 2006

(86) PCT No.: PCT/GB2006/001618
§ 371 (c)(1),
(2), (4) Date: Jun. 22, 2009

(87) PCT Pub. No.: WO2006/117557
PCT Pub. Date: Nov. 9, 2006

(65) Prior Publication Data
US 2009/0275063 A1    Nov. 5, 2009

(30) Foreign Application Priority Data

May 3, 2005  (GB) .................................. 0508981.8

(51) Int. Cl.
*C12Q 1/22* (2006.01)
(52) U.S. Cl. ................... 435/31; 435/23; 435/34
(58) Field of Classification Search .............. 435/31, 435/23, 34
See application file for complete search history.

(56) References Cited

U.S. PATENT DOCUMENTS 6,949,351 B1 *  9/2005  Squirrell et al. ............... 435/15

FOREIGN PATENT DOCUMENTS

| WO | WO 94/17202 | 8/1994 |
|---|---|---|
| WO | WO 96/02665 | 2/1996 |
| WO | WO 99/23489 | 5/1999 |
| WO | WO 00/46357 | 8/2000 |
| WO | WO 00/70082 | 11/2000 |
| WO | WO 02/092843 | * 11/2002 |
| WO | WO 2004/090089 | 10/2004 |

OTHER PUBLICATIONS

Balows, A.; "Current Techniques for Antibiotic Susceptibility Testing" 1974; ISBN 0-398-02886-9; Cover, copyright and contents pgs only (3 pgs.).
Baquero, F.; "European Standards for Antibiotic Susceptibility Testing: Towards a Theoretical Consensus"; Eur. J. Clin. Microbiol. Infect Dis.; vol. 9, No. 7; Jul. 1990; p. 492-495.
Baselski, V.; "The Role of Molecular Diagnostics in the Clinical Microbiology Laboratory"; DNA Technology—Clinics in Laboratory Medicine; vol. 16, No. 1; Mar. 1996; pp. 49-60.
Bean, P. et al.; "Differential Lysis of Tumor Target Cells Displayed by Lymphokine Activated Killer (LAK) Cell Clones"; International Journal of Cell Cloning; 10:190-195 (1992).
Blasco, R. et al.; "Specific assays for bacteria using phage mediated release of adenylate kinase"; Journal of Applied Microbiology; 84:661-666 (1998).
Dowd, S. et al.; "PCT Amplification and Species Determination of Mirosporidia in Formalin-Fixed Feces after Immunomagnetic Separation"; Applied and Environmental Microbiology; vol. 64, No. 1; Jan. 1998; pp. 333-336.
Fraser, F. et al.; "Topology of carnitine palmitoyltransferase I in the mitochondrial outer membrane"; Biochem. J.; 323:711-718 (1997).
Hornes, E. et al. ; "Detection of *Escherichia coli* Heat-Stable Enterotoxin Genes in Pig Stool Specimens by an Immobilized, Colorimetric, Nested Pllymerase Chain Reaction"; Journal of Clinical Microbiology; vol. 29, No. 11; Nov. 1991; p. 2375-2379.
Kassimi, L. et al.; "Detection of Encephalomyocarditis virus in clinical samples by immunomagnetic separation and one-step RT-PCR"; Journal of Virological Methods; 101:197-206 (2002).
Konstantivova, Doki Akad Nauk SSSR 203:1204-1206 (1972).
Li, Z. et al.; "Rapid Detection of *Mycobacterium avium* in Stool Samples from AIDS Patients by Immunomagnetic PCR"; Journal of Clinical Microbiology; vol. 34, No. 8; Aug. 1996; pp. 1903-1907.
Perrier, V. et al.; "Genetically Engineered Zinc-chelating Adenylate Kinase from *Escherichia coli* with Enhanced Thermal Stablity"; The Journal of Biological Chemistry; vol. 273; No. 30; Jul. 24, 1998; pp. 19097-19101.
Sanders, M.; "A Rapid Bioluminescent Technique for the Detection and Identification of *Listeria monocytogenes* in the Presence of *Listeria innocua*"; Bioluminescence and Chemiluminescence—Fundamentals and Applied Aspects; pp. 454-457 (1994).
Shetab, R. et al.; "Detection of *Bacteroides fragilis* Enterotoxin Gene by PCR"; Journal of Clinical Microbiology; vol. 36, No. 6; Jun. 1998; pp. 1729-1732.
Smaill, F.; "Antibiotic susceptibility and resistance testing: An overview"; Can J. Gastroenterol; vol. 14, No. 10, Nov. 2000; pp. 871-875.

(Continued)

*Primary Examiner* — Ralph Gitomer

(57) ABSTRACT

A method for detecting the absence or presence of cells of interest in a liquid sample is provided. The method comprises providing a sample suspected of containing cells of interest that contain an intracellular enzyme with a measurable activity. The sample further comprises an extracellular medium that also includes an extracellular enzyme with the measurable activity. The method further comprises the steps of treating the liquid sample with a reagent that inactivates the measurable activity in the extracellular medium but does not inactivate the measurable activity in the cells of interest, lysing the cells of interest to release the intracellular enzyme, and measuring the measurable activity. Thus, the measurable activity of the intracellular enzyme can be measured without interference from the extracellular enzyme. The invention is particularly useful for treatment of bacterially-infected blood using a detection assay based on adenylate kinase activity.

13 Claims, 15 Drawing Sheets

OTHER PUBLICATIONS

Squirrell, D. et al.; "Adenylate Kinase as a Cell Marker in Bioluminescent Assays"; Bioluminescence and Chemiluminescence—Fundamentals and Applied Aspects; pp. 486-489 (1994).

Zhang, G. et al.; "Rapid and Sensitive Assay for Detection of Enterotoxigenic *Bacteroides fragilis*"; Journal of Clinical Microbiology; vol. 36, No. 12; Dec. 1998; p. 3545-3548.

Sakakibara, T. et al.; "Enzymatic Treatment to Eliminate the Extracellular ATP for Improving the Detectability of Bacterial Intracellular ATP"; Analytical Biochemistry; 250:157-161 (1997).

Du, H. et al.; "Hybridization-Based Unquenching of DNA Hairpins on Au Surfaces: Prototypical "Molecular Beacon" Biosensors"; J. Am. Chem. Soc.; vol. 125; No. 14; 2003; p. 4012-4013.

* cited by examiner

FIGURE 3
FIGURE 3A
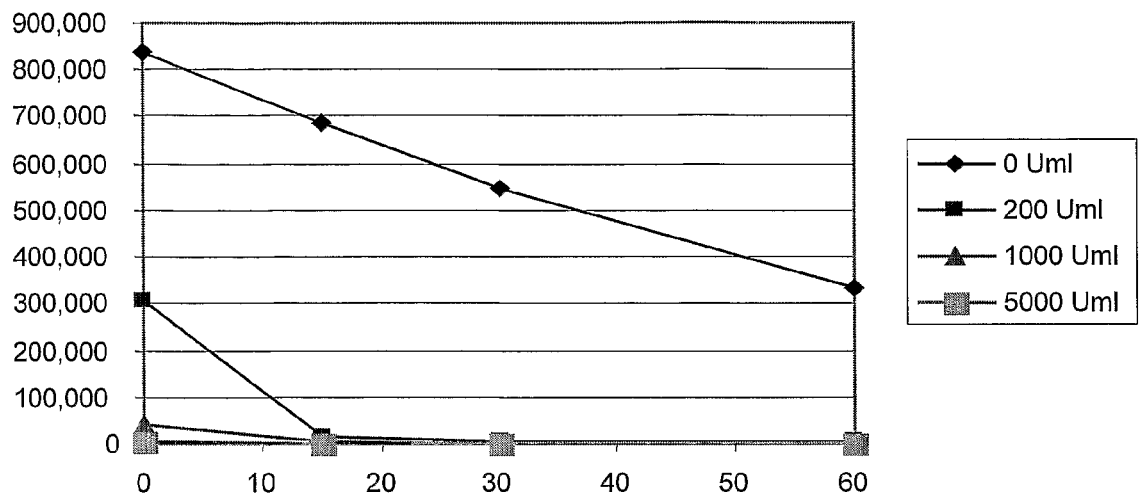
FIGURE 3B
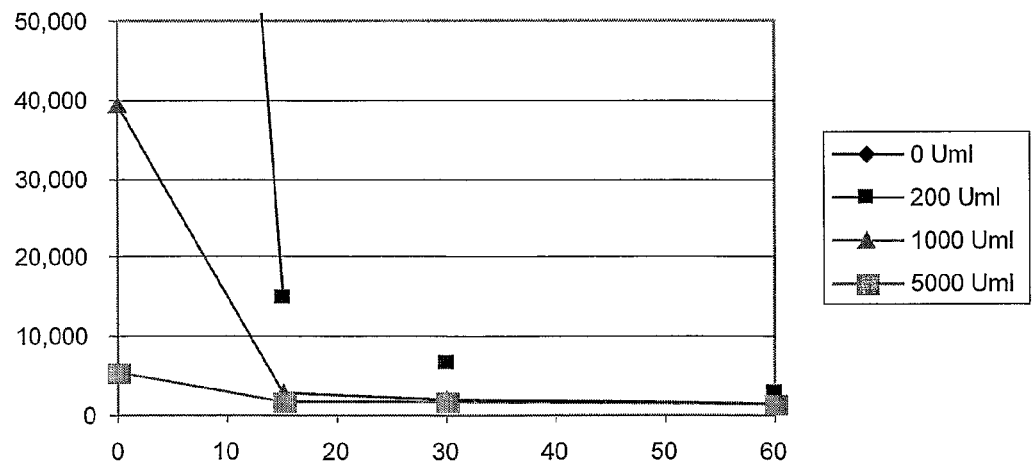

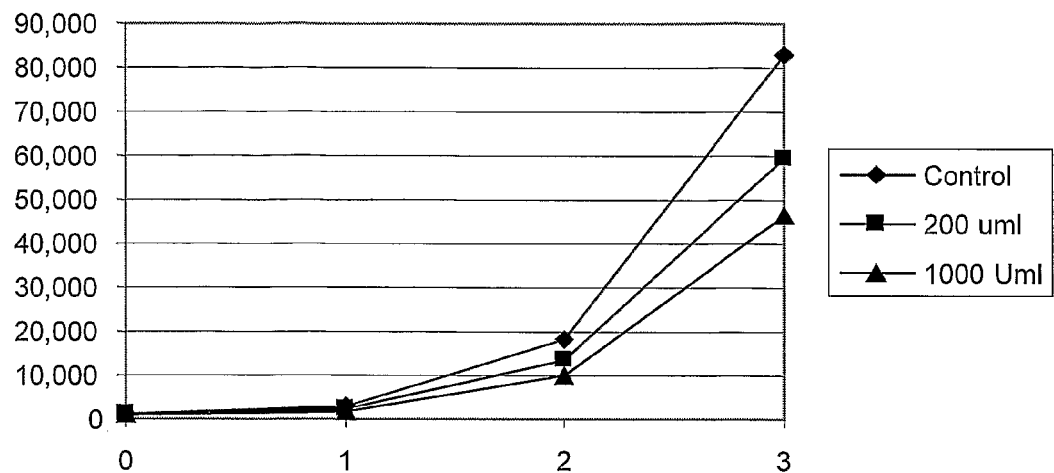
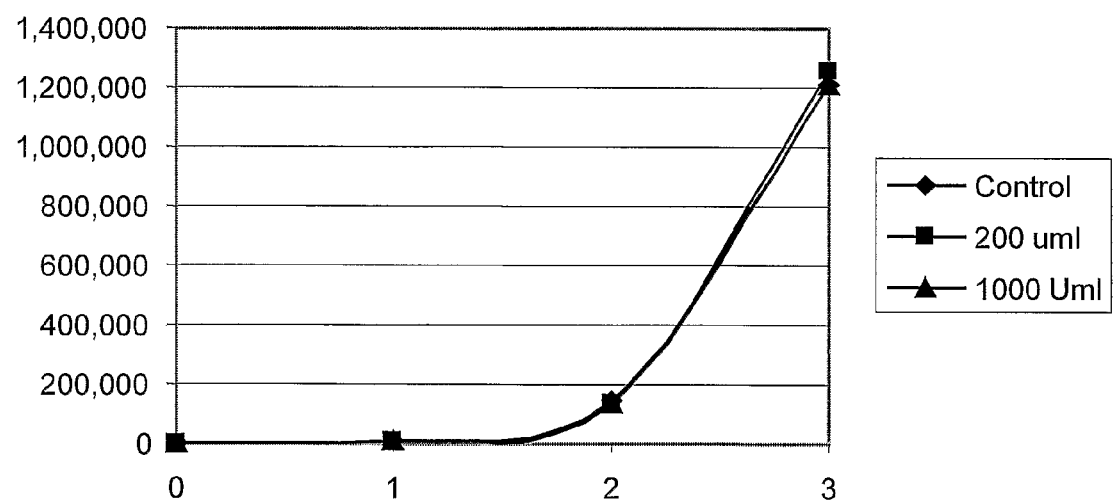

DISTINGUISHING CELLS IN A SAMPLE BY INACTIVATING EXTRACELLULAR ENZYME BEFORE RELEASING INTRACELLULAR ENZYME

All documents cited herein are incorporated by reference in their entirety.

The present application is a U.S. National Stage Application of PCT/GB2006/001618, filed May 3, 2006. The application also claims the benefit under 35 U.S.C. §119 of foreign application no. GB 0508981.8, filed May 3, 2005.

TECHNICAL FIELD

This invention is in the field of cell analysis, in particular for clinical diagnostic microbiology.

BACKGROUND ART

Clinical microbiology frequently involves the detection of bacteria in bodily fluids. As well as containing bacteria, these bodily fluids may contain cells from the patient themselves. The relative proportions of host and pathogen cells can vary widely e.g. a urine sample may contain many bacteria (>100,000 per ml) but few host cells, whereas a blood sample may contain a large ($10^7$ or more) excess of host cells.

Whereas some diagnostic tests can readily distinguish between host cells and bacterial cells (e.g. Gram staining, PCR), others cannot. For instance, some diagnostic tests rely on markers that are also present in host cells, and so the presence of both types of cell can interfere with the test. This sort of interference is found in gingival crevicular fluid (GCF) testing. Proteins such as alkaline phosphatase, acid phosphatase and lactate dehydrogenase have been found to be elevated in GCF samples in diseased states, but all of these enzymes can come from the host or from bacteria [1].

For situations where bacterial cells must be identified within a large background of host cells, but where a non-specific intracellular marker is being used, there is a need for a way of distinguishing the bacterial marker from the host background. More particularly, where a marker of interest within a clinical blood sample could be derived from a blood cell, a bacterial cell, or even from serum, there is a need to distinguish these various sources from each other.

DISCLOSURE OF THE INVENTION

The inventors have discovered a way of specifically detecting an intracellular microbial marker in a sample, even where the sample also contains that marker within host cells and/or in free solution. By using differential cell lysis, to lyse the host cells but leave the microorganisms intact, the host cell marker is released, and the marker in bulk solution is then inactivated. Lysis of the microorganisms releases the marker which, following inactivation of marker derived from the host cell and solution, can now be assayed without interference. This technique can be used not only for microorganisms in a host cell background, but for any mixture of cell types where the cells can be subjected to differential lysis.

Thus the invention provides a method for detecting the absence or presence of cells of interest in a liquid sample, wherein:
 (a) the sample: (i) comprises an extracellular medium containing an enzyme with a measurable activity; and (ii) is suspected of containing cells of interest that contain an intracellular enzyme with said measurable activity;
 (b) the method comprises the steps of: (i) treating the liquid sample with a reagent that inactivates said measurable activity in the extracellular medium, but does not inactivate the measurable activity in said cells of interest; (ii) lysing said cells of interest to release the intracellular enzyme; and (iii) measuring said measurable activity.

Detection of measurable activity in step (iii) indicates that cells of interest were present in the sample; conversely, absence of measurable activity indicates that cells were absent.

After inactivation of the extracellular activity, but before lysis in step (ii) of (b), cells of interest may be cultured to allow them to grow.

In a typical embodiment, the method of the invention will involve treating a composition resulting from selective lysis (e.g. a blood sample in which blood cells have been lysed but microorganisms are left intact) with a protease that digests the measurable enzyme. For example, the human adenylate kinase (AK) enzyme has been found to be susceptible to trypsin treatment, such that background AK activity in blood can be removed before microorganism lysis, and a microorganism's own AK activity can then be used for assay purposes without interference from blood AK. The method is particularly advantageous as the inventors have found that it allows microbial enzyme activity to be detected even though a sample initially contains a huge excess of the same activity in blood.

Thus the invention provides a method for detecting the absence or presence of a microorganism in a blood sample, comprising the steps of: (i) treating the blood sample with a reagent that lyses blood cells in the blood sample, but does not lyse any microorganisms in the blood sample, thereby releasing adenylate kinase from said blood cells; (ii) treating this lysate with a protease in order to inactivate adenylate kinase in the blood sample without inactivating adenylate kinase in the microorganisms; (iii) lysing the microorganisms to release adenylate kinase; and (iv) measuring adenylate kinase activity released by the microorganisms. Between steps (ii) and (iii), some or all of the microorganisms may be cultured to allow them to grow, and may be subjected to potential antimicrobial treatment(s).

The invention also provides a kit comprising a protease, and at least one (e.g. 1, 2, 3, 4, 5, 6, 7) of the following reagents: ADP; a soluble salt of a divalent metal cation; a luciferase; a luciferin; a saponin; an antifoaming agent; and/or an anticoagulant. The divalent metal cation is preferably $Zn^{++}$ or $Mg^{++}$. The antifoaming agent is preferably polypropylene glycol. The anticoagulant is preferably polyanetholsulphonate. The saponin is a preferred component. The kit preferably includes each of: ADP; a soluble salt of a divalent metal cation; a luciferase; and a luciferin.

The invention also provides a reaction vessel comprising a lysis reagent and a protease. The vessel is typically a disposable tube, and is suitable for receiving a blood sample for performing a one-step blood lysis and adenylate kinase inactivation procedure. The invention also provides the reaction vessel further comprising blood cells (which will typically be lysed).

The Measurable Enzymatic Activity

The invention relies on the presence of a measurable enzymatic activity in cells of interest. The enzymatic activity is not specific to the cells of interest, however, and can thus suffer interference from other sources of that activity. The invention therefore inactivates that activity in an extracellular medium, then releases intracellular enzymes with that activity, such that the activity of the released enzyme can be measured without interference from the now-inactivated extracellular enzyme.

The inactivated enzyme and the released enzyme have the same measurable activity, but they need not be the same enzyme. For instance, the enzymes may be isoenzymes (isozymes) such that they catalyse the same reaction, even though they may have different enzymatic parameters (such as $K_M$ and $k_{cat}$). In all cases, however, the enzymes share an activity which is to be measured in an assay, such that the presence of both enzymes would interfere in the results of the assay.

For detecting bacterial cells, various enzymatic activities can be used. Rather than use an activity that is unique to bacteria, however, the invention uses an activity that is also seen in a other organisms, such as in animal cells (and particularly blood cells) or plant cells. Suitable enzymatic activities include those which are ubiquitous, such as activities of the glycolytic pathways, transcription, etc.

Lactate dehydrogenase (LDH) is found in many body tissues especially heart, liver, kidney, skeletal muscle, brain, blood cells (including red cells, white cells and platelets), and lungs and is involved in basic cellular metabolism. There are several LDH isoenzymes, all of which are present in serum. LDH is also found in microorganism. Thus a blood sample can contain three sources of LDH: serum; human intracellular; and microbial intracellular. The invention allows the microorganism LDH activity to be distinguished from the serum and human intracellular LDH activity. LDH is a convenient activity for use with the enzyme because assays for LDH activity in blood are already readily available as part of standard blood pathology tests.

References 2 to 7 disclose a method for detecting cells based on the release of intracellular adenylate kinase (AK) after cell lysis. AK is found in blood cells and in microorganisms, as well as in serum, but the invention advantageously allows the microbial AK activity to be distinguished from the serum and human intracellular AK activity. Removal of unwanted background AK activity has been reported in reference 8 using denaturation by heat, extreme pH, extreme salt concentrations or ultrasound. These methods are unsuitable for use with the present invention, however, as they may destroy the cells of interest, or else they may be reversible when conditions revert to normal, in which case the interfering activity returns.

The most preferred enzymatic activity used with the invention is AK activity. AK has EC number E.C.2.7.4.3, and has also been known as myokinase, adenylic kinase and adenylokinase. It can catalyse the production of ATP and AMP from two ADP molecules, transferring phosphate from one ADP onto the other, and can also catalyse production of ATP from ADP and Pi. The enzyme uses a divalent metal cation, and typically a magnesium ion or zinc ion. With a source of ADP and $Mg^{++}/Zn^{++}$, therefore, AK can generate ATP from exogenous ADP. This reaction is very efficient, and a single AK enzyme can catalyse the production of 400,000 molecules of ATP from ADP in 10 minutes. The methods of the invention may therefore involve adding ADP and a source of a suitable divalent cation. The molar concentration of the cation is preferably the same as or greater than the molar concentration of ADP such that all ADP molecules can be associated with at least one cation.

ATP can be conveniently detected using a luciferase reaction. Using AK to generate ATP from exogenously-added ADP is over 100-fold more sensitive than the use of endogenous ATP to drive the luciferase reaction, and also shows better correlation with cell numbers. Thus the combination of AK and luciferase can be used as a quantitative measure of cell numbers. The methods of the invention may therefore involved adding luciferin and luciferase during or, preferably, after the generation of ATP, optionally followed by determining the amount of luciferase-generated light emitted from the sample. Thus AK activity is measured indirectly, via the luciferase reaction.

The Cells of Interest

The method of the invention allows cells of interest to be detected against a background of other cells, even though an enzyme marker is used that is common to both cell types. The invention achieves this differential detection by lysing interfering cells, inactivating marker that is released in the lysis step, and then lysing the cells of interest.

Preferred cells of interest are bacteria, including but not limited to: Staphylococci, such as *S. aureus* (and more particularly methicillin-resistant *S. aureus*, or 'MRSA'); Enterococci such as *E. faecium* and *E. faecalis* (and more particularly vancomycin-resistant *E. faecalis*); Streptococci such as *S. pyogenes, S. pneumoniae* (and more particularly penicillin-resistant *S. pneumoniae*), and *S. agalactiae*; Coliforms such as *E. coli, Klebsiella* species (e.g. *K. oxytoca*), *Proteus* species (e.g. *P. vulgaris*), and *Enterobacter* species (e.g. *E. cloacae*); Enteric organisms like *Salmonella* species (e.g. *S. enteritidis*), *Shigella* species, and *Campylobacter* species; *Neisseria* species such as *N. meningitidis, N. gonorrhoeae*; *Acinetobacter* species such as *A. baumanii*; *Serratia*, such as *S. marcescens*; *Pseudomonas*, such as *P. aeruginosa*; and specific pathogens such as *Burkholderia cepacia, Bacillus anthracis, Clostridium botulinum, Yersinia pestis, Corynebacterium diphtheriae* and *Boidetella pertussis*. The invention can also be used with yeasts, such as *C. albicans*. It can also be used with parasites such as *P. falciparum, Leishmania*; spirochaetes; schistosoma; etc. This list is not exhaustive, but serves to illustrate the wide range of disease-causing microorganisms which can be detected using the invention.

The Liquid Sample

The invention can be used with various liquid samples that might contain cells of interest that share a label of interest e.g. blood samples, semen samples, urine samples, faeces, food samples, etc. The invention is most useful for detecting bacterial cells in blood. Thus the liquid sample used in the method of the invention will typically be a blood sample. The blood sample may be direct from a patient, or may have been treated e.g. heparinised, centrifuged, lysed, etc. The blood sample may be intended for transfusion.

Blood comprises serum and cells. Both the serum and cells may contain the enzyme activity of interest (e.g. LDH is present within both blood cells and serum). Both of these sources can interfere with an assay of that activity in microorganisms, and the invention can remove both sources at the same time by lysing the blood cells such that the blood-bound marker is released. A typical liquid sample for analysis by the method of the invention will thus be a blood sample in which blood cells have been lysed, but any microorganisms have been left intact. This sample thus comprises (i) an extracellular medium comprising serum and a blood cell lysate, and (ii) any microorganisms that were present in the original sample.

Methods for preferentially lysing blood cells (including red cells, white cells and platelets) in a sample, leaving microbial cells intact, are well known in the art, particularly from clinical microbiological analysis systems and parasitic blood infection diagnosis, and include methods such as saponin lysis, the use of RB buffers, and the use of surfactants and osmotic shock. The Isolator™ system from Oxoid™ utilises reagents that lyse leucocytes and erythrocytes in blood without harming bacteria, and is based on the use of purified saponin. Polypropylene glycol is also used, to block the foaming tendency of saponins, and sodium polyanetholsulphonate acts (i) as an anticoagulant (ii) to neutralise the bactericidal properties of blood and (iii) to inhibit phagocytosis. RB buffers are well known in the art (e.g. 40 mM MOPS, 10 mM sodium acetate, 1 mM EDTA, pH 7.0; or 0.5 mM $MgCl_2$, 1 mM EGTA, and 0.1 M MES-KOH, pH 6.8) and are used in the 'microLYSIS™ for Infected Blood' system sold by Cambio (Cambridge, UK) and Microzone (Haywards Heath, UK). If white cells need not be lysed then RB buffer can be replaced by TE buffer. Preferably the blood cells are lysed using a saponin. Preferably platelets are lysed using a non-ionic surfactant, such as, for example Triton™ X-100 and/or M-Per.

Further examples of differential lysis methods include, but are not limited to: red and white blood cells can be differentially lysed using the methods disclosed in reference 9; activated killer (LAK) cell clones can differentially lyse tumour cells [10]; in forensic science analysis, differential lysis is used to distinguish sperm cells from other cells, particularly from epithelial cells.

Inactivation of the Enzyme

The method of the invention involves a step in which a liquid sample is treated with a reagent that inactivates an enzymatic activity. The inactivation method does not, however, inactivate the measurable activity in cells of interest that are also present in the liquid sample. Thus the activity in the cells of interest can be measured at a later stage in the method.

For selective inactivation of extracellular activity, without inactivating intracellular activity, methods such as heat denaturation [8] will generally not be used, as they will also destroy the activity within cells of interest. Rather, chemical or physical methods will be used, and typical inactivation methods will use a reagent that can act on extracellular material but cannot enter intact cells. Selectivity thus arises from impermeability to the reagent of the membrane of a cell of interest.

The inactivation is preferably irreversible. Thus treatment with inhibitors, mild chemical denaturants, etc. is not preferred.

The reagent that inactivates the enzyme activity may or may not kill the cells of interest. For a test where microorganisms extracted from blood will subsequently be grown (e.g. for antimicrobial susceptibility testing), a non-lethal inactivating reagent should be used.

One class of reagent is acids and bases. Addition of acid has been found to inactivate extracellular AK. However, pH should not be reduced or increased so severely that the measurable enzyme within the cells of interest is also denatured (or, where living cells of interest are required after inactivation, so severely that the cells die). After inactivation, and before or during lysis of the cells of interest, pH should be adjusted to avoid inactivation of released enzyme.

A preferred irreversible treatment involves the use of a proteolytic enzyme. Suitable proteases include, but are not limited to: trypsin; chymotrypsin; bromelain; elastase; papain; pepsin; rennin; plasminogen; subtilisin; thrombin; pancreatin; cathepsin; ficin; proteinase K etc. Proteases such as trypsin, papain, chymotrypsin, proteinase K, pepsin and rennin are preferred, because they are widely and cheaply available. The ability of a particular protease to inactivate a marker enzyme of choice can be determined by routine biochemical assays and/or, where sequence information is available, can be predicted based on the amino acid sequence of the target and the recognition sequence of the protease. Should a particular protease not be effective in a particular circumstance (e.g. see references 11 & 12), an alternative protease can readily be found. Proteases with specific properties can also be chosen for specific circumstances e.g. choosing proteases that are thermostable, that have a very low or high pH optimum, that can tolerate the presence of a particular compound, etc.

The inventors have found that inactivation of serum AK and AK released from blood cells can conveniently be achieved, without killing microorganisms or inactivating their AK, by the use of trypsin. Trypsin has previously been used to digest (and thus inactivate) AK for biochemical studies (e.g. reference 13), but its use for selective inactivation of extracellular AK has not been reported. Contrary to expectations, trypsin has been found not to harm blood-borne bacteria (they retain the ability to grow even after the treatment), and it is believed that this resilience may result from not having to maintain the bacteria in minimal growth media. Moreover, trypsin has been found not to inactivate AK located within the bacteria. Furthermore, trypsin does not significantly interfere with downstream AK assays and so does not need to be removed after microbial lysis, as long as the AK/luciferase assay proceeds soon thereafter. The AK/luciferase assay is rapid enough to give full results within 5-10 minutes, and the effect of trypsin on microbial AK over this timescale is negligible. Even so, the effect of trypsin on microbial AK can advantageously be further minimised by (a) adding a trypsin inhibitor and/or (b) changing the pH or and/or temperature away from trypsin's optimum but towards the AK/luciferase optimum and/or (c) including in the lysis reagent a chemical that inactivates trypsin.

The pH optimum of a protease may be the same as, similar to (e.g. within 2 pH units of) or different from (e.g. more than 2 pH units away from) the pH optimum of the enzyme to be measured after lysis. By choosing a protease with a different pH optimum (e.g. an enzyme with a pH optimum below 5.5 or above 10 when using the AK/luciferase reaction), and by adjusting pH to match the measurable enzyme's optimum (e.g. adjusting before or during lysis of the cells of interest), it is possible to reduce the risk that the protease may inactivate enzyme released from the cells. Thus the use of an enzyme such as pepsin (pH optimum in the range 2-4) may be used to inactivate an enzyme such as AK, then pH can be adjusted to be suitable for AK assay (e.g. around 7.5), and cells can be lysed to release their AK in the presence of the pepsin, but the pepsin will not be active.

Inactivation with a protease will generally involve simple mixing of the sample with the protease, followed by incubation to allow proteolytic digestion to proceed. Incubation conditions may be chosen to match the preferences of the protease (e.g. pH, temperature, ions, buffers, etc.), but these conditions should not be changed so much that the intracellular enzyme is irreversibly inactivated, or such that a cell of interest is killed if downstream steps require otherwise e.g. although a particular protease may have a temperature optimum of 55° C., a cell of interest may not tolerate this temperature, and so a lower temperature should be used as a compromise. Before or during protease digestion, therefore, the method of the invention may involve temperature adjustment and/or pH adjustment. As mentioned above, temperature and/or pH can also be adjusted at the end of protease digestion, and/or a protease inhibitor can be added, to prevent further proteolytic digestion. Inhibitors of proteases are well known and are readily available e.g. BPTI, etc.

The concentration of protease used for inactivation will depend on various parameters, including the concentration of enzyme to be digested, the time available for the inactivation, the time required for the downstream assay (during which the protease may still be present), etc. These parameters can be chosen and optimised without difficulty. Digestion for up to 12 hours is typical e.g. up to 6 hours, up to 4 hours, etc.

Antimicrobial Susceptibility Testing

The method of the invention is well-suited to antimicrobial susceptibility testing (AST) [14 to 16] on microorganisms extracted from patient samples.

In one embodiment, the cells of interest are extracted, and these extracted cells are used for the AST testing. In another embodiment, the patient sample is cultured, with multiple extractions of cells. In both embodiments, an increase in measurable activity over time means that microorganism growth is increasing, indicating the presence of an infection. The first embodiment is preferred.

In the first embodiment, the invention provides a method for detecting the absence or presence of cells of interest in a liquid sample, wherein:
  (a) the sample: (i) comprises an extracellular medium containing an enzyme with a measurable activity; and (ii) is suspected of containing cells of interest that contain an intracellular enzyme with said measurable activity;
  (b) the method comprises the steps of: (i) treating the liquid sample with a reagent that inactivates said measurable activity in the extracellular medium, but does not inactivate the measurable activity in said cells of interest; (ii) establishing a culture of the cells of interest that remain after step (i); and (iii) taking one or more samples from said culture.

The samples taken in step (iii) of (b) can each be subjected, as described herein, to lysis of cells of interest (e.g. bacteria) to release the intracellular enzyme (e.g. AK), and then measurement of said measurable activity. Samples taken in step (iii) can be treated with antimicrobials for AST assays. If samples are tested at different times, an increase in activity over time indicates growth of the cells. The samples taken in step (iii) may also, or alternatively, be subjected to a process for identifying the microorganisms (if any) that are present.

In the second embodiment, a patient sample is incubated under conditions that permit microorganism growth, and sub-samples can be removed at n different times (where n is an integer of 2 or more e.g. 2, 3, 4, 5, 6, 7, 8, 9 or 10). Each sub-sample is subjected to inactivation, lysis and measurement. Thus the invention provides a method for detecting the absence or presence of cells of interest in a liquid sample, wherein:
  (a) the sample: (i) comprises an extracellular medium containing an enzyme with a measurable activity; and (ii) is suspected of containing cells of interest that contain an enzyme with said measurable activity;
  (b) the method comprises the steps of: (i) incubating the sample under conditions that permit microorganism growth; (ii) taking a first sub-sample from the sample at a first time point; (iii) treating the first sub-sample with a reagent that inactivates said measurable activity in its extracellular medium, but does not inactivate the measurable activity in said cells of interest; (iv) lysing said cells of interest to release the intracellular enzyme; (v) measuring said measurable activity; (vi) taking a second sub-sample from the sample at a second time point; (vii) treating the second sub-sample with a reagent that inactivates said measurable activity in its extracellular medium, but does not inactivate the measurable activity in said cells of interest; (viii) lysing said cells of interest to release the intracellular enzyme; and (ix) measuring said measurable activity,
  wherein an increase in measurable activity between said first time point and said second time point indicates growth of said cells of interest between said time points.

These methods can be used for antimicrobial susceptibility testing by performing the method on parallel samples, one of which is treated with an antimicrobial agent. The untreated sample serves as a control, indicating normal growth in the sample; in the sample treated with antimicrobial agent, microorganism growth can be compared to the control growth, and a lower growth rate (including no growth, or even a decrease) indicates that the microorganisms are susceptible to the antimicrobial agent, and treatment decisions for a patient can be made accordingly. This procedure is illustrated in FIG. 1, and it can be performed in parallel for a panel of antimicrobials.

To determine whether microorganism numbers are rising, falling or remaining static over time, it is preferred to use a quantitative technique. The AK/luciferase assay meets this requirement.

The invention can similarly be used to generate a killing curve, in which the effect of an antimicrobial at a given concentration is followed over time.

If antimicrobials are tested at various concentrations, the invention can be used to identify minimum inhibitory concentration (MIC) values for antimicrobials (i.e. the lowest concentration of a particular antimicrobial which can inhibit the growth of a given microorganism) or minimum bactericidal concentration (MBC) values (i.e. the lowest concentration which can kill a given microorganism).

According to the invention, a plurality of antimicrobials can be tested (e.g. 2, 3, 4, 5, 6, 7, 8, 9, 10, 15, 20 or more). Furthermore, a plurality of concentrations of each antimicrobial can preferably be tested (e.g. 2, 3, 4, 5, 6, 7, 8, 9, 10, 15, 20 or more), and preferably between 4 and 8 (e.g. 6). It is preferred to test a range of concentrations in the range from 0.05 to 150 mg/ml, more preferably a range from 0.125 to 16 mg/l, or even up to 128 mg/ml. The range preferably spans the known break-point for an antimicrobial.

In general, for a single AST, MIC or MBC test, the method of the invention may involve: adding an antimicrobial at a pre-determined concentration to a sample; incubating the sample in the presence of the antimicrobial for a pre-determined time period (e.g. a period which would allow $\geqq 2$ logs of growth in the absence of antimicrobial); and assessing the number of micro-organisms in the sample at the end of said time period.

For a complete AST test, the method of the invention may involve: adding a plurality of different antimicrobials at pre-determined concentrations to a plurality of different sub-samples; incubating the sub-samples in the presence of the antimicrobials for pre-determined time periods; and assessing the numbers of micro-organisms in the sub-samples at the end of said time periods.

For a complete MIC or MBC test, the method of the invention may involve: adding an antimicrobial at a plurality of pre-determined concentrations to a plurality of different sub-samples; incubating the sub-samples in the presence of the antimicrobial for pre-determined time periods; and assessing the numbers of micro-organisms in the sub-samples at the end of said time periods.

For killing curve testing, the method of the invention may involve: adding an antimicrobial at a pre-determined concentration to a sub-sample; incubating the sub-sample in the presence of the antimicrobial for a pre-determined time period; and assessing the number of micro-organisms in the sub-sample at a plurality of time points within said time period.

Tests may include a step of determining the number of micro-organisms in a sub-sample at time zero. In the first embodiment, this may take place before, during or after establishment of the culture.

The method of the invention may further comprise the step of using the results of the antimicrobial testing step to calculate a MIC and/or MBC value for a given micro-organism in a patient sample. MIC values may be presented as true MICs, abridged MICs, or calculated MICs.

As explained above, antimicrobial testing will typically be accompanied by a control analysis in which a micro-organism is incubated in the absence of antimicrobials. In addition, the process of the invention may include control tests. Typical negative controls could be to perform the method on basic culture medium, etc.

In general, assessment of micro-organism numbers in a sample taken at a specific time will not be performed immediately. A typical process will thus require the inhibition of further growth in a sub-sample once an assessment is to be made. Further growth can be inhibited by addition of "stop solution" such as an azide, by cooling or rapid freezing, by lysis, etc.

Incubation steps preferably take place at a predetermined temperature e.g. at 37±2° C. Higher temperatures may be used if desired e.g. at 41° C. the doubling time of $E. coli$ is 7 minutes, compared to 20 minutes at 37° C., so higher temperatures can accelerate analysis. Higher temperatures are also useful for some slow-growing organisms. The temperature preferences of different microorganisms are well known in microbiology and temperatures used in the invention can be modified accordingly.

The term "antimicrobial" refers to any substance (typically an organic compound) that can kill, or inhibit the growth of, a micro-organism. The term includes natural and synthetic compounds. It includes antibiotics, antimycotics and antivirals within its scope, with antibiotics being a preferred subset of antimicrobials. Classes of antimicrobials which may be tested include beta-lactams, aminoglycosides, fluoroquinolones, sulfonamides, glycopeptides, carbapenems, azoles, oxazolidinones, macrolides, quinolones, tetracyclines, etc. Typical antimicrobials for use with the invention are: penicillin, amoxycillin, ciprofloxacin, cephalothin, ampicillin, augmentin, linezolid, gentamicin, flucluxacillin, vancomycin, chloramphenicol, tetracycline, minocycline, sulfonamide, oxazolidinone, fluconazole, nitrofurantoin, trimethoprim, nalidixic acid, amphotericin, kanamycin, streptomycin, vidarabine, acyclovir, gancyclovir, AZT (zidovudine), 3TC (lamivudine), etc.

The invention may also be used to test the effect of mixtures of two or more antimicrobials. Testing combinations may identify positive or negative synergies between the antimicrobials against a particular extracted micro-organism.

Different antimicrobials typically have different activity profiles e.g. they may be slow- or quick-acting. Each antimicrobial test may therefore be different. As the invention involves the use of known antimicrobials, however, the invention can be adapted according to the profile of any particular antimicrobial.

If an antimicrobial is used that is specific to a particular type of microorganism (e.g. is specific for Gram negative bacteria, or is a lysin or phage specific for a particular organism, such as lysostaphin) then the post-inactivation lysis can take place in stages e.g. a first stage where a first subset of the cells of interest is lysed and assayed, and a second stage where a second subset of the cells of interest is lysed and assayed, etc. Thus different cell types that remain after the initial lysis and inactivation can be distinguished, again by relying on specific lysis.

Further Method Steps

As well as including steps of treating a liquid sample to inactivate the measurable activity, lysing the cells of interest to release the intracellular enzyme and measuring the released activity, methods of the invention can include further steps.

As mentioned above, before cells of interest are lysed, they may be cultured to increase cell numbers. Different organisms typically have different optimum growth conditions (media, aerobic/anaerobic, temperature, etc.). For example, streptococci grow well in Todd-Hewitt medium, whereas $S. aureus$ prefers peptone. The invention may thus utilise a number of different conditions but, for simplicity, it is preferred to compromise by using 'generic' media e.g. BHI (brain heart infusion). The choice of growth medium will ultimately depend on the choice of micro-organisms to be assayed and such choices are familiar to workers in this field. The choice of growth medium may depend on geographical location e.g. the EU and USA have different standard methodologies.

The methods of the invention may include a step of microorganism identification e.g. in order to determine the type of microorganisms in a sample prior to AST. This identification may be based on phenotype (e.g. on morphology, growth characteristics, etc.), but genotype-based techniques are now available [17] which allow a micro-organism to be identified on the basis of nucleic acid sequence (e.g. use of PCR has been widely described [e.g. refs. 18 to 23]), and these techniques are rapid, sensitive and specific.

Prior to lysing cells of interest, the methods of the invention may involve measuring the measurable activity. Thus the number of blood cells in a sample could also be determined, for example.

Following lysis, nucleic acid may be captured on a solid support for analysis. The solid support may be the particle used for initial separation, or may be a separate support. The nucleic acid may be DNA, RNA or any naturally occurring or synthetic modification thereof, and combination thereof. Preferably however the nucleic acid will be DNA, which may be single or double stranded or in any other form, e.g. linear or circular. If it is desired to remove RNA from DNA, this may be achieved by addition of an RNase or an alkali such as NaOH.

The invention also provides a method for screening a blood sample (e.g. one intended for blood transfusion) for the presence of a pathogen, comprising the step performing a method of the invention on the sample. If the method gives a negative result (i.e. the cells of interest are not present) then the blood sample can be cleared for transfusion; if it gives a positive result (i.e. the cells of interest are present) then the blood sample can be rejected for transfusion. In screening, it may not be important to identify the specific pathogen that is present, as the presence of any pathogen means that the sample should be rejected.

Partial Methods

Where a method of the invention includes the three basic steps of inactivation, lysis and measurement, these can take place at different times and places. For instance, a blood sample might be taken and inactivated by a physician in the field, or in a hospital. Growth and measurement of microorganisms can then take place in a laboratory elsewhere.

Thus the invention provides a method for detecting the absence or presence of cells of interest in a liquid sample, wherein:

(a) the sample: (i) comprises a liquid sample that has been treated with a reagent that inactivates a measurable activity in the extracellular medium, but does not inactivate the measurable activity in said cells of interest; and (ii) is suspected of containing cells of interest that contain an intracellular enzyme with said measurable activity;

(b) the method comprises the steps of: (i) lysing said cells of interest to release the intracellular enzyme; and (ii) measuring said measurable activity.

Similarly, the invention provides a method for treating a liquid sample, wherein:

(a) the sample: (i) comprises an extracellular medium containing an enzyme with a measurable activity; and (ii) is suspected of containing cells of interest that contain an intracellular enzyme with said measurable activity;

(b) the method comprises the step of: (i) treating the liquid sample with a reagent that inactivates said measurable activity in the extracellular medium, but does not inactivate the measurable activity in said cells of interest.

Similar partial methods of the invention will be apparent.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an enzyme is described as being "intracellular", this term is generally used to mean "not extracellular", in the sense that the enzyme is not accessible during inactivation to inactivating reagents that are located extracellularly. An intracellular enzyme may be variously located within a cell, including on the inner face of a cell's outer membrane, on the outer surface of the outer membrane but protected during inactivation e.g. by an organism's capsule, in an inner membrane, in the periplasm, in an organelle, etc.

BRIEF DESCRIPTION OF DRAWINGS

FIGS. 2 and 3 show the decrease in AK activity when incubated with trypsin. FIG. 2 shows bacterial AK activity, and FIG. 3 shows AK activity in lysed blood. FIG. 3B is an enlargement of the bottom part of FIG. 3A.

FIGS. 4 to 14 show bacterial growth in the presence of AK. Bacteria were: (4) *E. coli*; (5) *E. faecalis*; (6) *P. aeruginosa*; (7) *S. aureus*; (8) *K. pneumoniae*; (9) *E. cloacae*; (10) *K. oxytoca*; (11) *P. vulgaris*; (12) *A. baumanii*; (13) *S. enteritidis*; and (14) *S. narcescens*.

The Y-axes in FIGS. 2 to 15 show 'RLU' (relative light unit) values. The X-axes show time in minutes (FIGS. 2 & 3) or hours (FIGS. 4-15).

Figure 16:
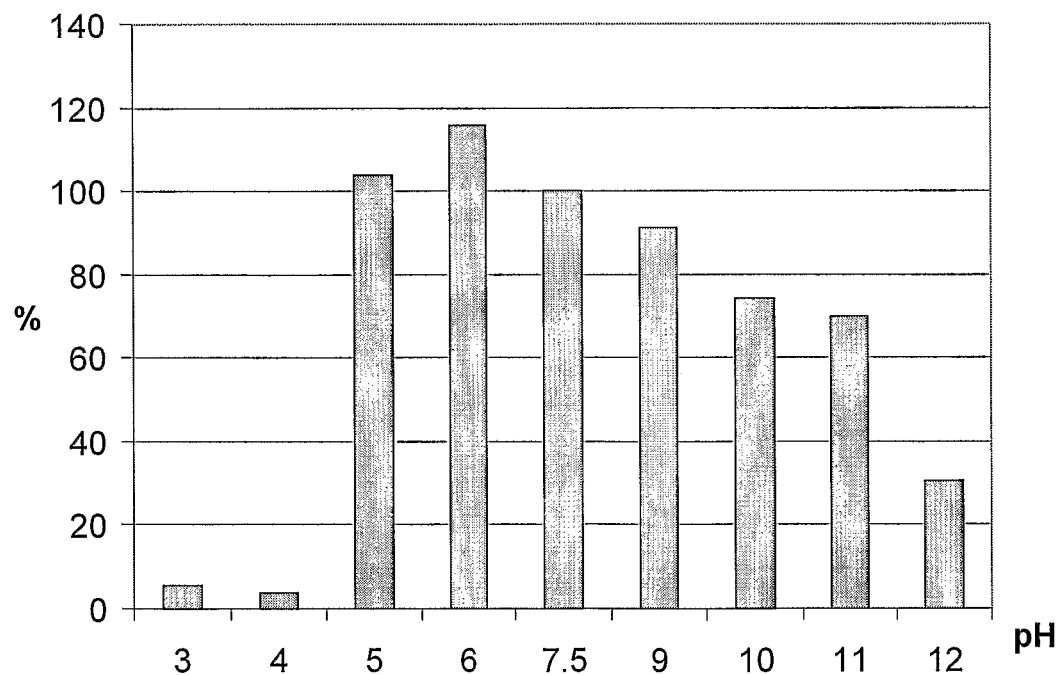

FIG. 16 shows the effect of pH on AK activity.

Figure 17:
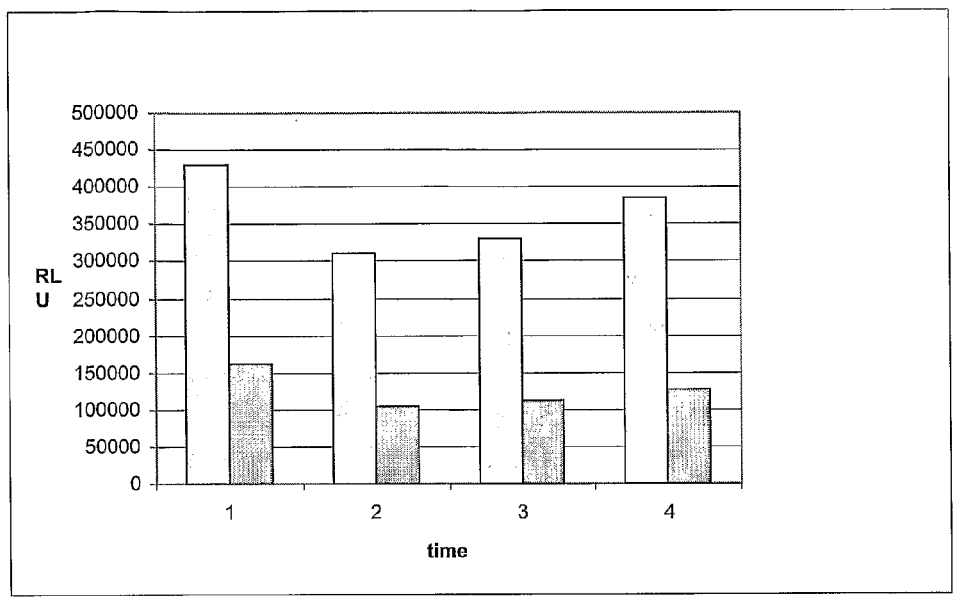

FIG. 17 shows the reduction of platelet AK activity caused by trypsin digestion and the change in AK activity over time. Light shading is platelets, dark shading is platelets+trypsin.

Figure 18:
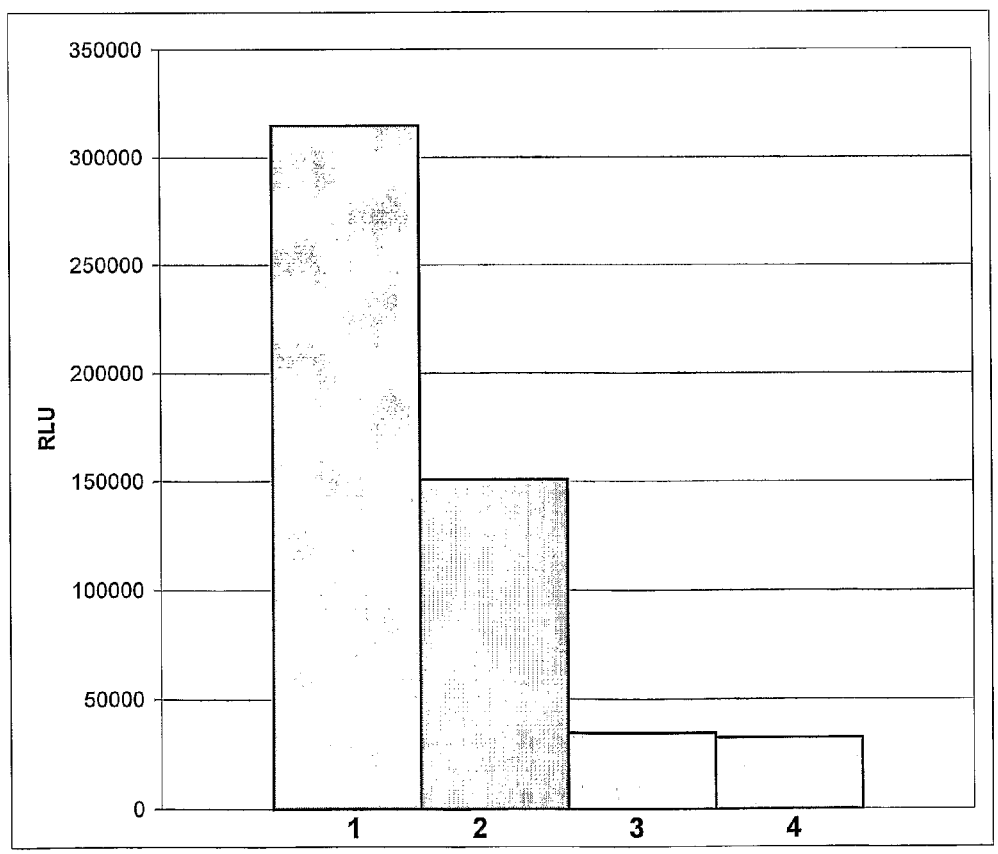

FIG. 18 shows the reduction of platelet AK activity caused by trypsin digestion and differing durations of centrifugation. 1=lysis with 1 min centrifugation, no trypsin; 2=lysis with 3 min centrifugation, no trypsin; 3=lysis 1 min, trypsin; and 4=lysis 3 min, trypsin.

FIGS. 19 to 24 show extracted adenylate kinase from different bacteria incubated with different proteases. The bacteria were: (19) *S. epidermis* (AC086), (20) *S. aureus* (AC082), (21) *E. coli* (AC024), (22) *E. faecalis* (AC012), (23) *P. aeruginosa* (AC044) and (24) MRSA (AC145).

FIG. 25 to 30 show the effects of different proteases on bacteria cultured in the presence of collistin, ciprofloxacin and oxacillin. The bacteria were: (25) *S. aureus* (AC082), (26) *S. epidermis* (AC086), (27) MRSA (AC145), (28) *E. coli* (AC024), (29) *P. aeruginosa* (AC044) and (30) *E. faecalis* (AC012).

The Y-axes in FIGS. 19 to 30 show 'RLU' (relative light unit) values normalised to t=0. The normalisation is carried out by dividing the mean value for each timepoint by the mean value at t=0. The X-axes show time in minutes.

MODES FOR CARRYING OUT THE INVENTION

Experimental work used adenylate kinase-generated ATP to drive a luciferin/luciferase activity, giving results in RLUs as a quantitative measure of initial ATP levels. All AK assays were performed at pH 7.5, and 37° C. Results of the assay were read at ambient temperature.

In preliminary experiments, adenylate kinase inactivation was performed by reducing pH. In later experiments, inactivation used porcine trypsin at pH 7.5. The pH reduction permanently inactivated blood AK, without affecting intracellular bacterial AK, but the use of trypsin was more efficient and less clumsy.

Thus, the current protocol used in the assay is:

Add 1 ml saponin/sps/ppg to 10 ml whole blood—allow to fully lyse (10-15 mins).

Centrifuge 5,000 rpm for 45 mins.

Remove Supernatant.

Prepare a 10× concentrate of trypsin (10,000 U/ml) stock in appropriate media (e.g. MH broth is generally used).

Resuspend pellet in 30-40 ml MH (a second centrifugation/resuspension ("wash") step for high background samples can be included here if required).

Add trypsin stock to final resuspension sample at 1/10 dilution (to give final concentration of 1,000 U/ml).

Incubate at 37° C. for duration of the required incubation step—typically 4-5 hours, but is dependent on bacterial growth rate.

Assay for AK activity (see below).

pH Reduction to Inactivate AK

To assess the effect of pH on AK activity, purified enzyme was incubated for 1 hour at various pH, with pH 7.5 being the control (normal assay conditions). AK activity was measured by using the bioluminescent luciferin/luciferase to detect AK-generated ATP. Results were as follows (FIG. 16):

| Incubation pH | 3 | 4 | 5 | 6 | 7.5 | 9 | 10 | 11 | 12 |
|---|---|---|---|---|---|---|---|---|---|
| RLU ($10^3$) | 15.7 | 11.1 | 299.0 | 333.5 | 288.2 | 262.4 | 214.5 | 201.2 | 88.6 |

In further experiments, three treatment conditions were tested: (i) a control, run at pH 7.5 with no pH change; (ii) a transient pH drop before the assay, where pH was reduced to pH 4 and then returned to pH 7.5; and (iii) an acidic incubation, where pH was reduced to pH 4 for 15 minutes. AK activity was then assessed. In parallel tests, the effect of these pH conditions on the viability of *E. coli* and *E. faecalis* was assessed. Results were as follows (%):

|  | Control | Transient pH drop | Acidic incubation |
|---|---|---|---|
| AK alone | 100 | 91 | 13 |
| *E. coli* | 100 | 89 | 83 |
| AK alone | 100 | 89 | 8 |
| *E. faecalis* | 100 | 86 | 67 |

Thus incubation at pH 4 can be used to substantially inactivate AK (e.g. in the order of a 10-fold reduction in activity) without causing substantial damage to the viability of bacteria in the same sample and without inactivating their intracellular AK. Acid conditions can thus be used to inactivate extracellular AK without destroying downstream assays of intracellular AK.

Trypsin Control

In preliminary experiments, the effect of trypsin on the bioluminescent system was assessed. Samples of trypsin at different concentrations, diluted in Mueller-Hinton ($MH^+$) broth, were spiked with ATP. Results were as follows:

| Sample | | RLU Mean |
|---|---|---|
| No ATP | Control (0 U/ml) | 392 |
| | 5000 U/ml | 414 |
| | 1000 U/ml | 538 |
| | 200 U/ml | 646 |
| +ATP | Control (0 U/ml) | 65,538 |
| | 5000 U/ml | 81,276 |
| | 1000 U/ml | 64,005 |
| | 200 U/ml | 68,036 |

Thus there is little or no background ATP-generating activity associated with trypsin, although at 5000 Units/ml (U/ml) the signal appears to be 'boosted'. At trypsin levels ≦1000 U/ml there is minimal/no effect on the bioluminescence reaction.

Trypsin Digestion of Intracellular Bacterial AK

Concentrations of $10^4$ and $10^5$ cfu/ml *E. coli* and *E. faecalis* where spiked into MH broth containing 1000, 200 and 0 (control) U/ml trypsin. These were assayed immediately. Results were as follows:

| Organism | cfu | | Trypsin conc | |
|---|---|---|---|---|
| | | | 200 | 1000 |
| | | | Mean RLU | |
| *E. coli* | $10^4$ | +trypsin | 7,197 | 12,694 |
| | | Control | 8,857 | 14,260 |
| | $10^5$ | +trypsin | 65,452 | 106,552 |
| | | Control | 77,690 | 127,808 |
| *E. faecalis* | $10^4$ | +trypsin | 13,310 | 17,369 |
| | | Control | 14,675 | 18,107 |
| | $10^5$ | +trypsin | 87,059 | 103,959 |
| | | Control | 93,758 | 111,965 |

Thus only approximately 10-20% of the AK signal generated from the lysed bacteria is lost during the AK reaction due to trypsin digestion.

AK Reduction by Trypsin Over Time

Purified AK (*B. stearothermophilus*) or a $10^{-3}$ dilution of saponin-lysed blood was incubated for 1 hour at 37° C. in 5000, 1000, 200 and 0 (control) U/ml trypsin diluted in MH broth ('trypsin/MH'). Aliquots were assayed at time 0, 15 minutes, 30 minutes and 1 hour.

Figure 1:
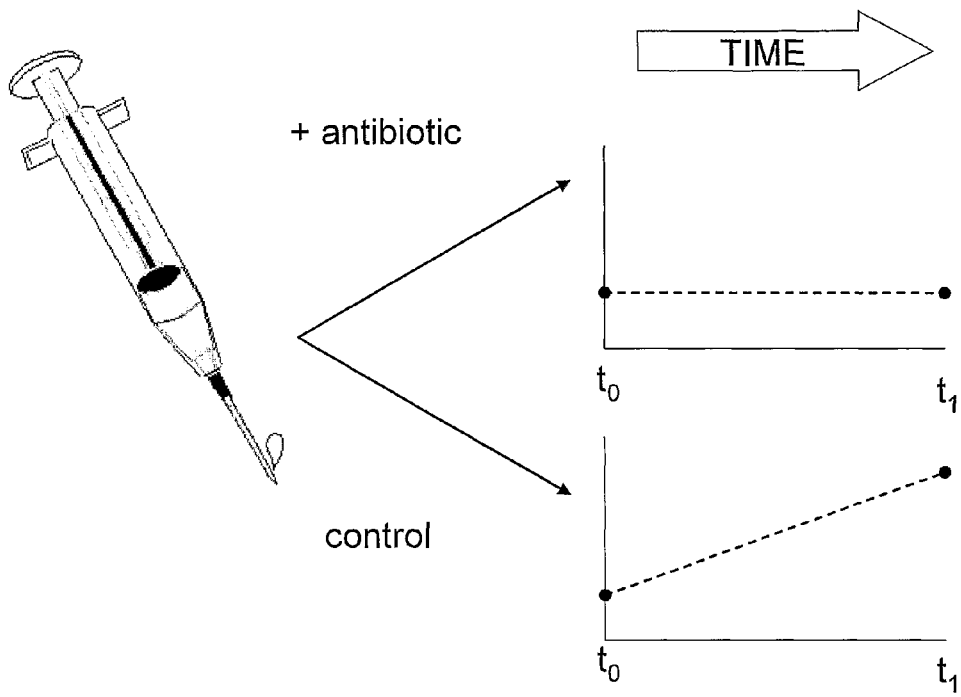
FIG. 1 illustrates application of the invention to antimicrobial susceptibility testing.
Figure 2:
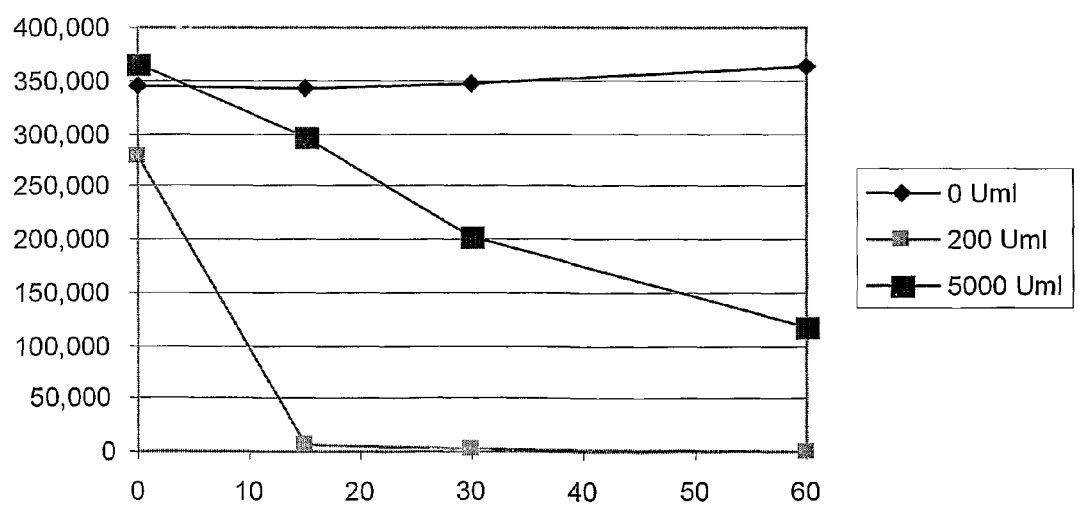
Figure 4:
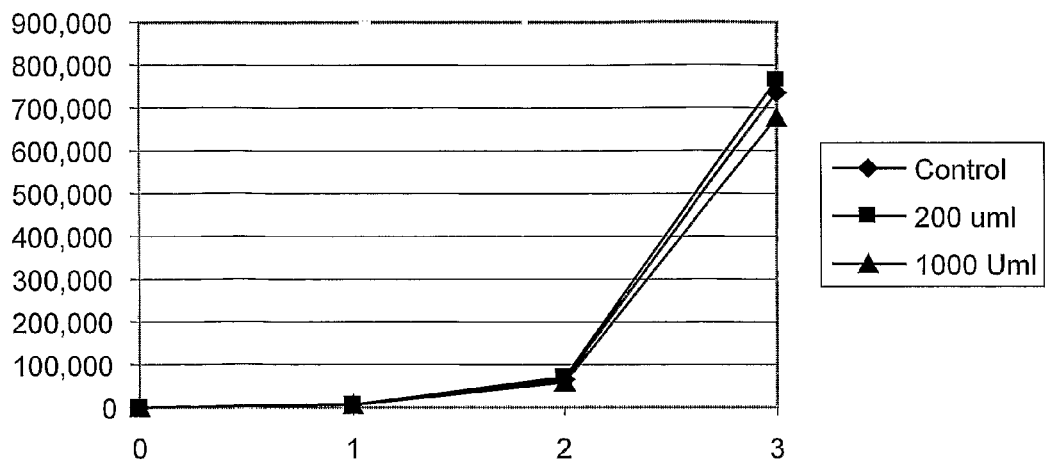
Figure 5:
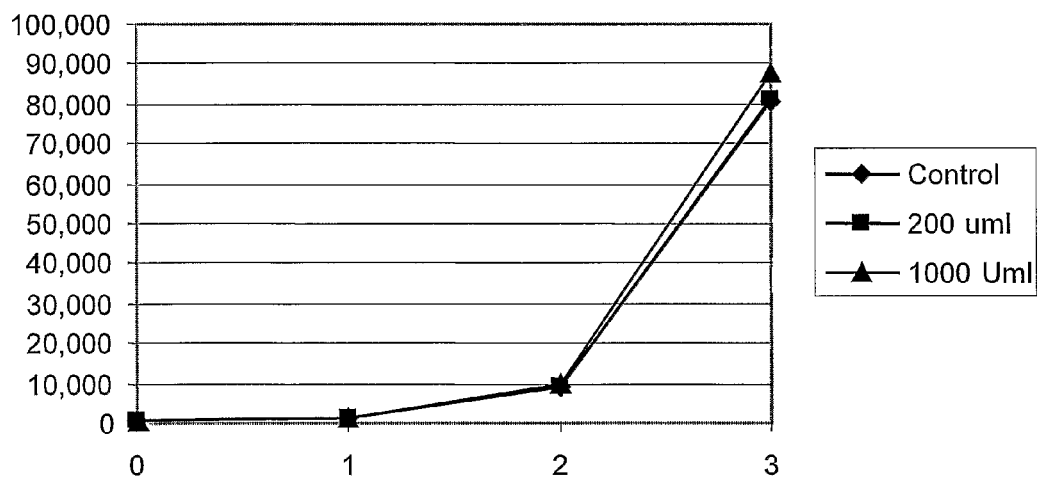
Figure 6:
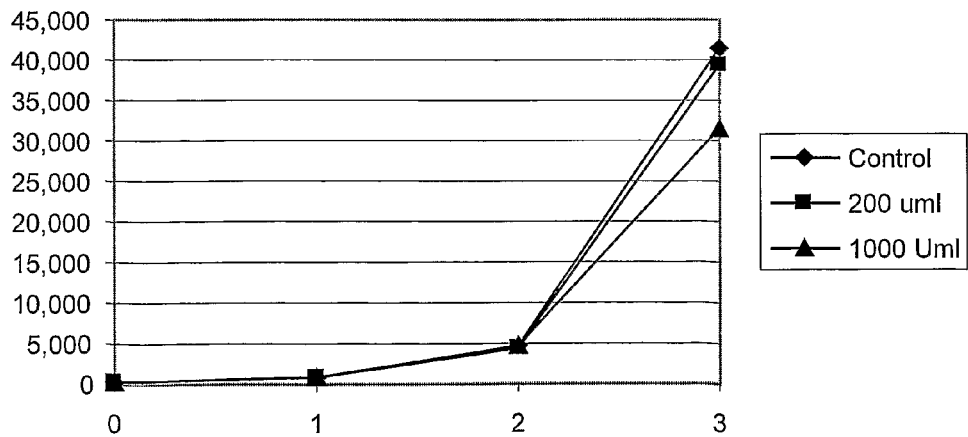
Figure 9:
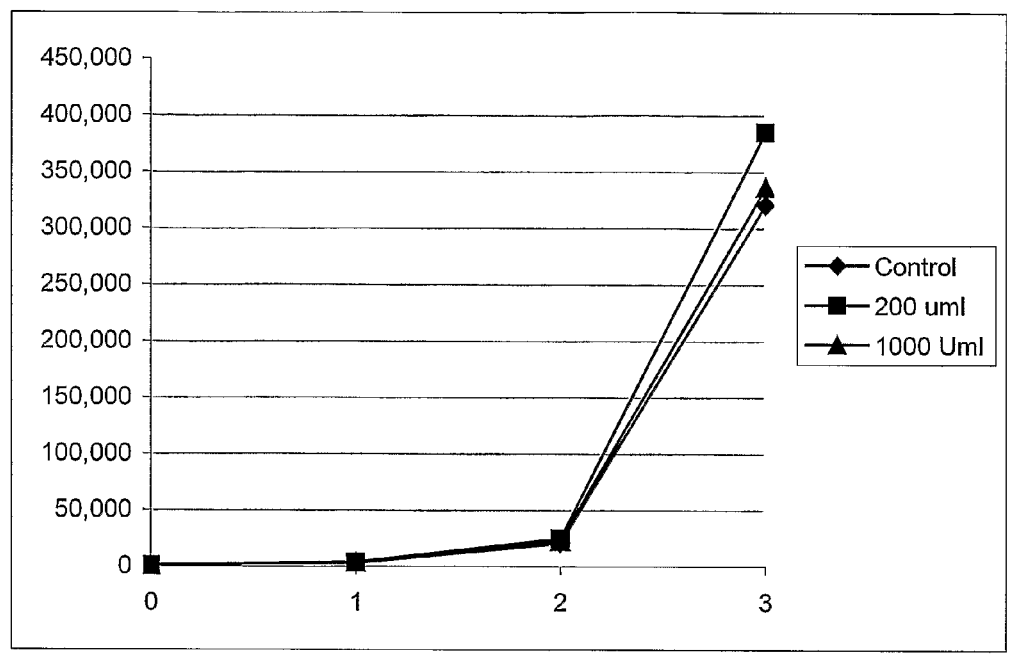
Figure 10:
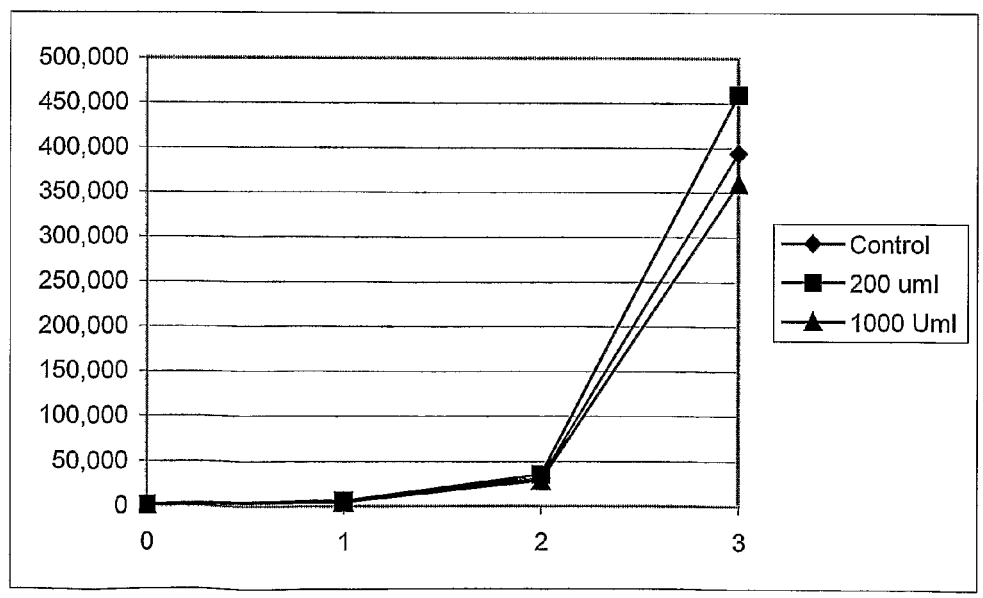
Figure 11:
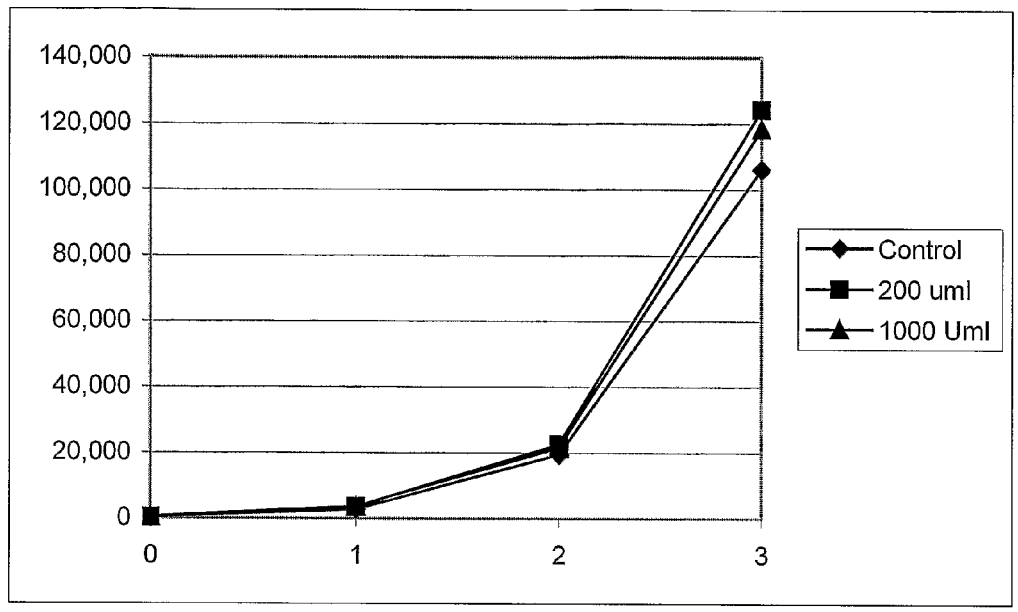
Figure 12:
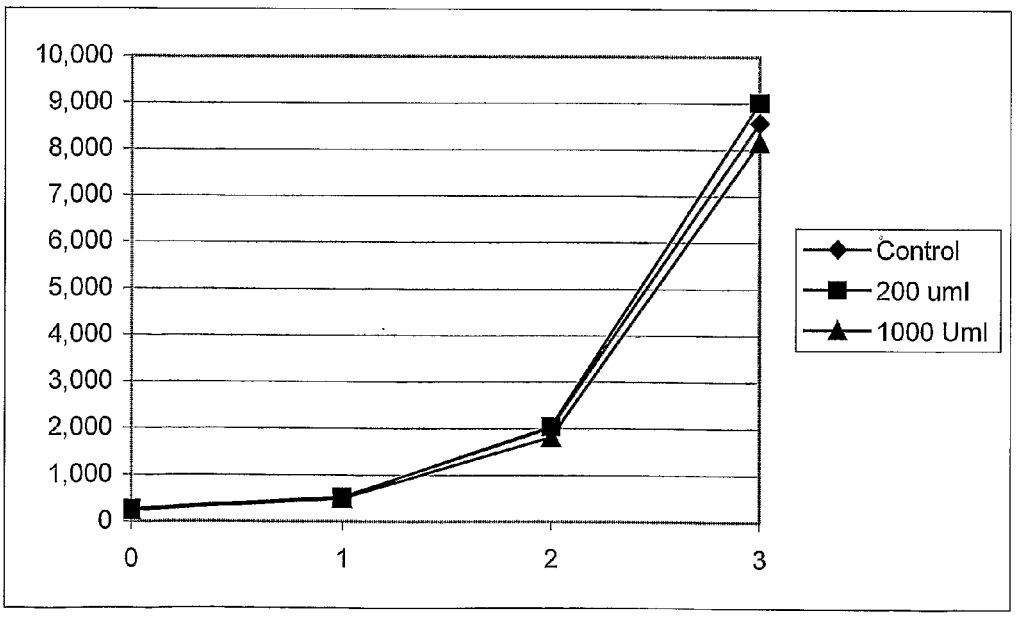
Figure 13:
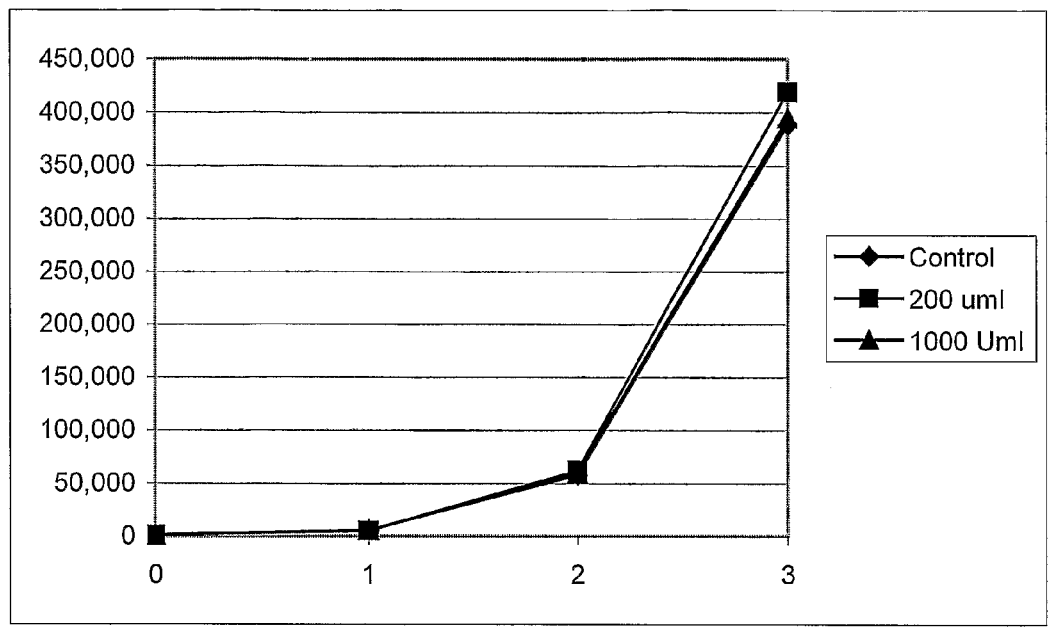
Figure 14:
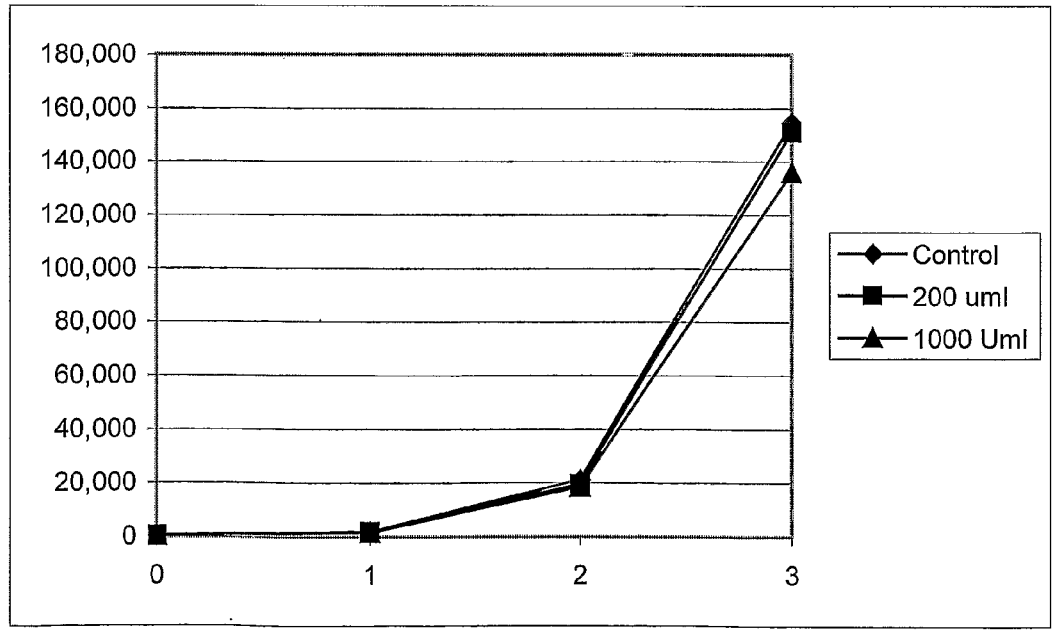

For the bacterial AK, the decrease in activity over time is shown in FIG. 2. With the lysed blood cells, the decrease in AK activity over time is shown in FIG. 3.

Thus AK in lysed blood is digested rapidly by trypsin. Even at time zero (i.e. length of time taken to aliquot and assay the samples) a large reduction in signal can be seen at the higher trypsin concentrations. Over time a lower plateau appears to be reached when trypsin is added to lysed blood, which is not evident with the purified bacterial AK, suggesting a small proportion of the AK in blood is inaccessible to the trypsin (e.g. inside unlysed cells). This plateau is also due to the presence of cellular ATP which is unaffected by proteases.

Degradation of AK in lysed blood occurs significantly more quickly than with purified bacterial AK. In addition, it has been discovered that AK from Gram −ve bacteria degrades more quickly than AK from Gram +ve bacteria. Although the bacterial AK is degraded, this does not occur as dramatically or rapidly as the AK from lysed blood. Coupled with the results given above, where bacterial AK is only reduced 10-20% after release from lysed bacteria, these data suggest that bacterial AK may be less susceptible to trypsin degradation than mammalian blood AK, offering further advantages when using trypsin to inactivate blood-derived AK without interfering with the intracellular bacterial enzyme. This effect may be related to the thermophilic nature of the source organism for the purified AK.

AK Reduction by Different Proteases Over Time for Different Organisms

Experiments were carried out in a similar manner to those described above and are described below.

Recovery and Testing of Bacterial Adenylate Kinase
1. Bacteria were scraped from plates and inoculated in approximately 20 ml of broth only. These were incubated overnight at 37° C.
2. 10× stocks of the enzymes were prepared in broth only:
    a. 10 mg of 16,000 U/mg Trypsin added to 16 ml of broth to give 10,000 U/ml (10×) stock.

b. 25 mg of 4 U/mg Papain added to 1 ml of broth to give 100 U/ml (10×) stock.
c. 10 mg of 7.5 U/mg proteinase K added to 3 ml of broth to give a 25 U/ml (10×) stock.
d. 10.5 ul of 239 U/ml chymotrypsin added to 239.5 ul of broth to give a 10 U/ml stock.
3. The inoculums were then centrifuged at approximately 14030 RCF for one hour.
4. The supernatant was then taken, tested for adenylate kinase activity (described below), and diluted with broth only if needed to give about $10^5$ cpm/ml.
5. The supernatant was then assayed for adenylate kinase activity at time point zero in triplicate and averaged.
6. 1.5 ml solutions of the supernatants were prepared with the correct concentration of enzyme, or broth for control. These were incubated at 37° C.
7. Samples were then taken and assayed in triplicate for adenylate kinase activity at 10, 30, 60 and 120 minutes.
8. The triplicates were averaged, and normalised by dividing by the time point zero average.

Adenylate Kinase Assay (AK Only No Cells)
1. 100 of sample added to a cuvette.
2. 50 µl of reagent 1 (ADP only; no lysis agent) added and vortexed briefly.
3. After 5 minutes, the cuvette was placed into a luminometer.
4. 50 µl of reagent 2 (dilution and luciferin/luciferase) firmly added directly to the sample.
5. RLU read immediately.

Figure 19:
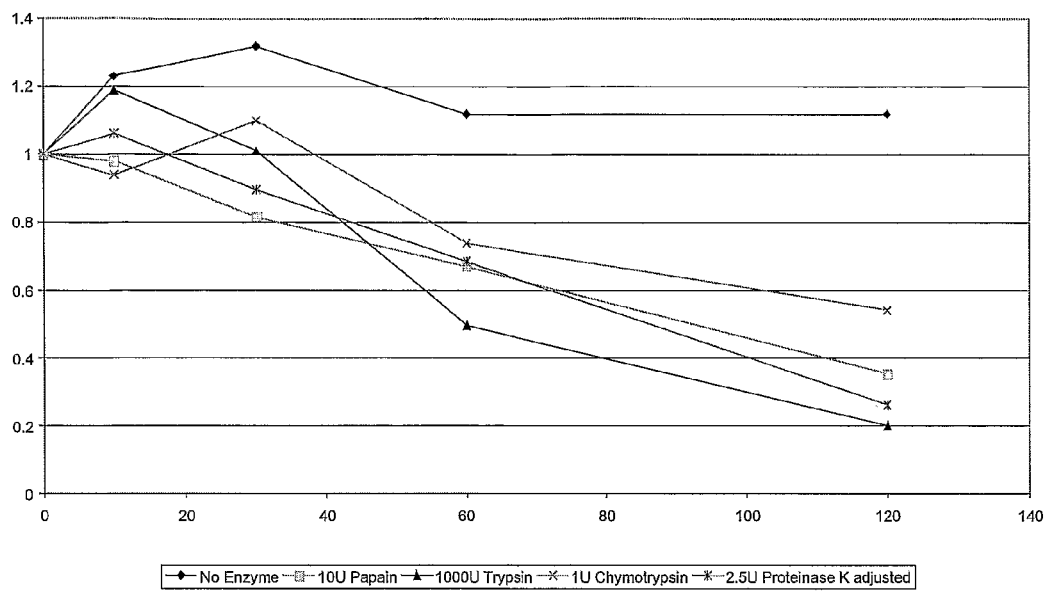
Figure 20:
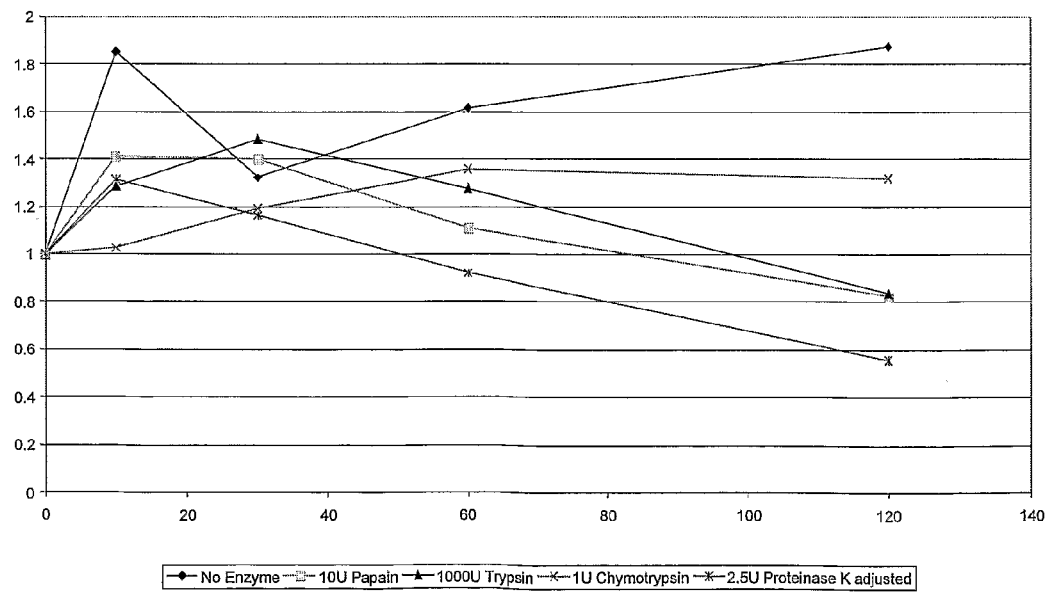
Figure 21:
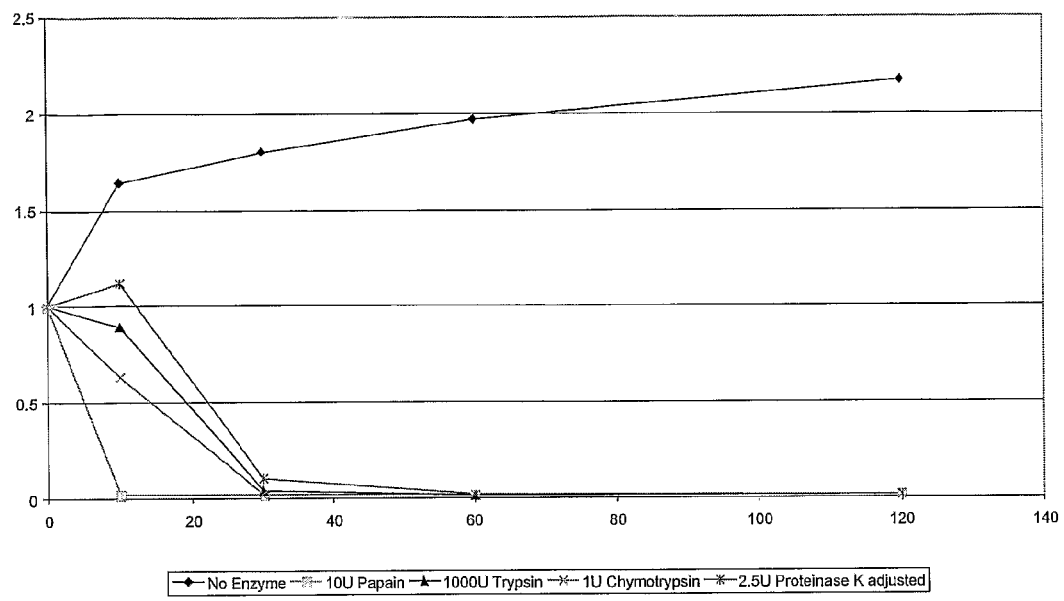
Figure 22:
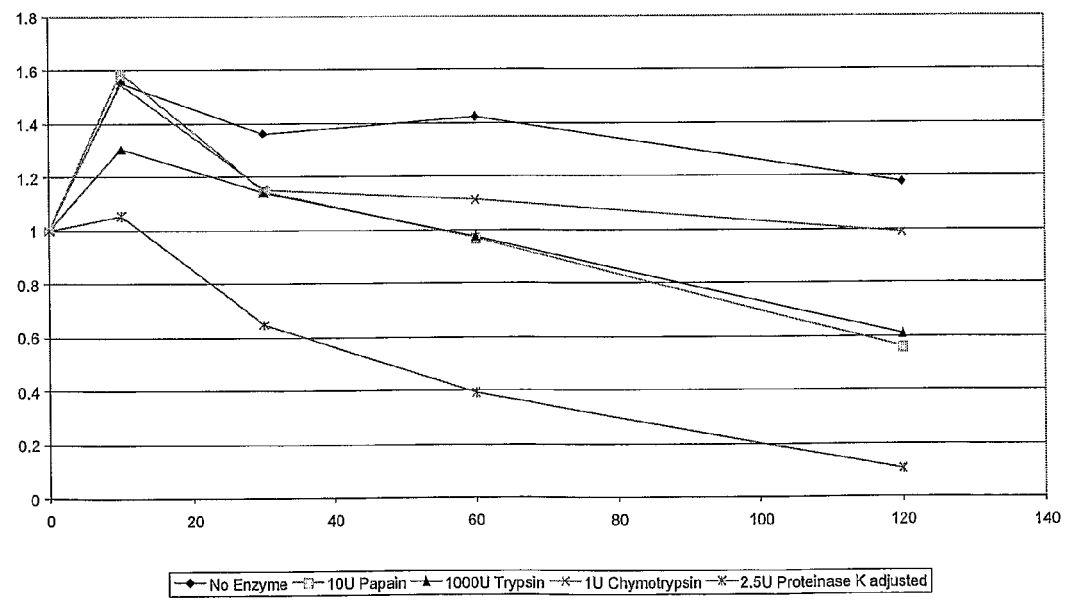
Figure 23:
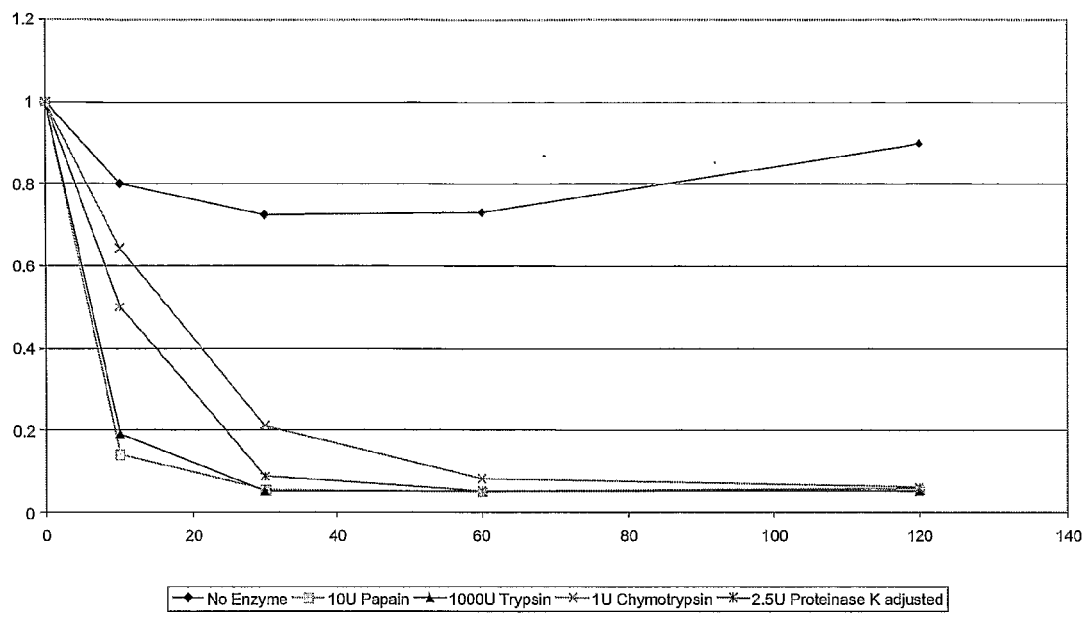
Figure 24:
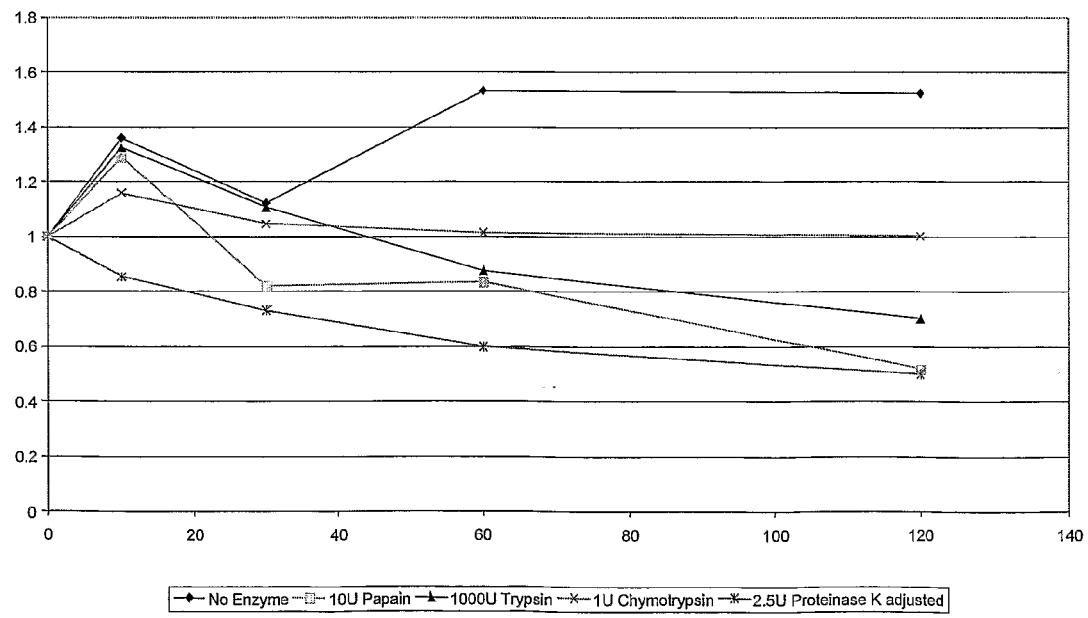
Figure 25:
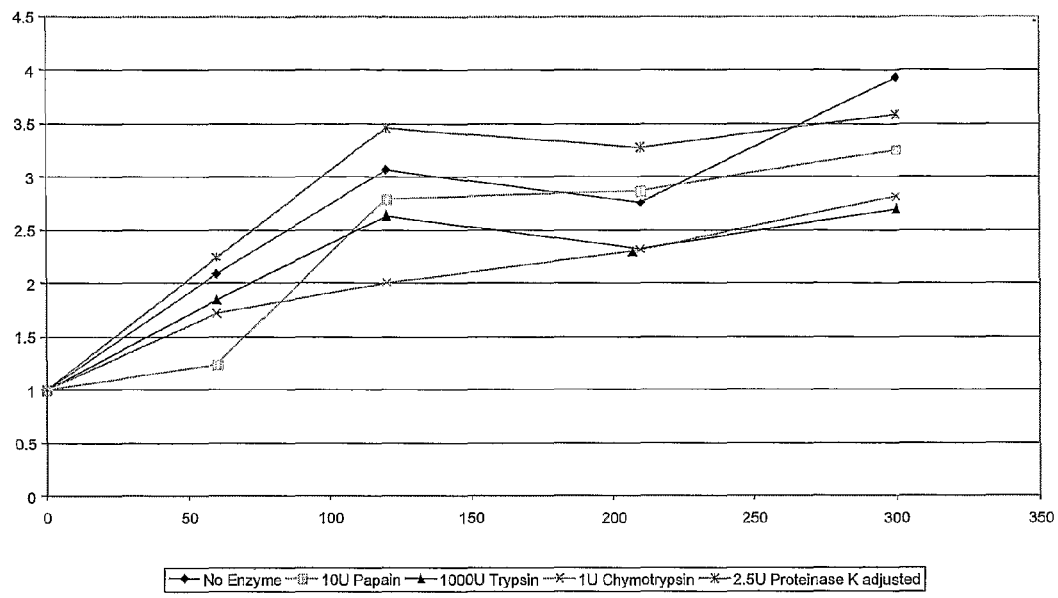
Figure 26:
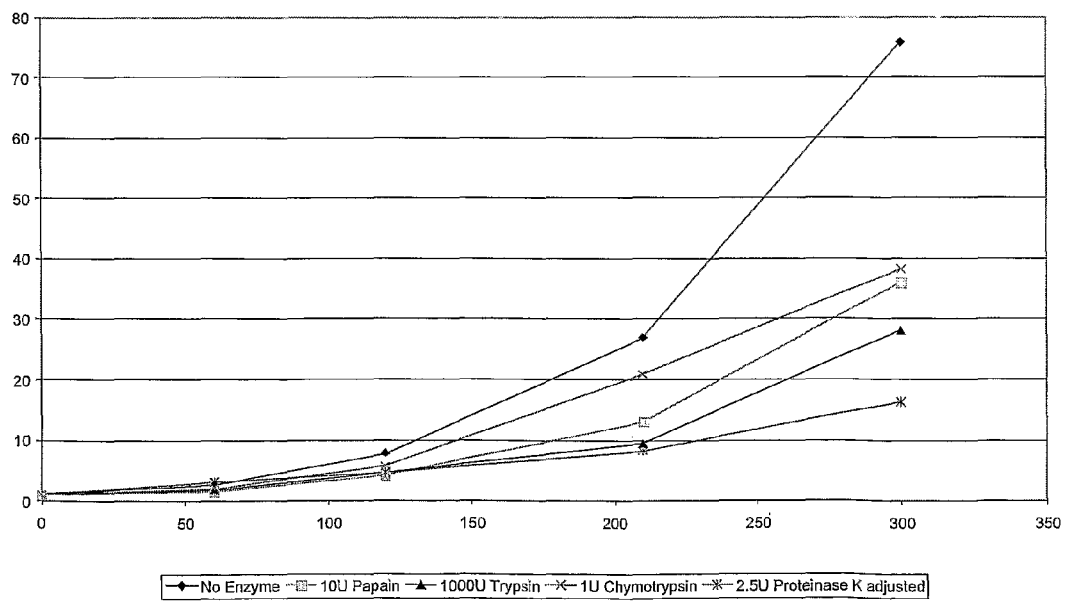
Figure 27:
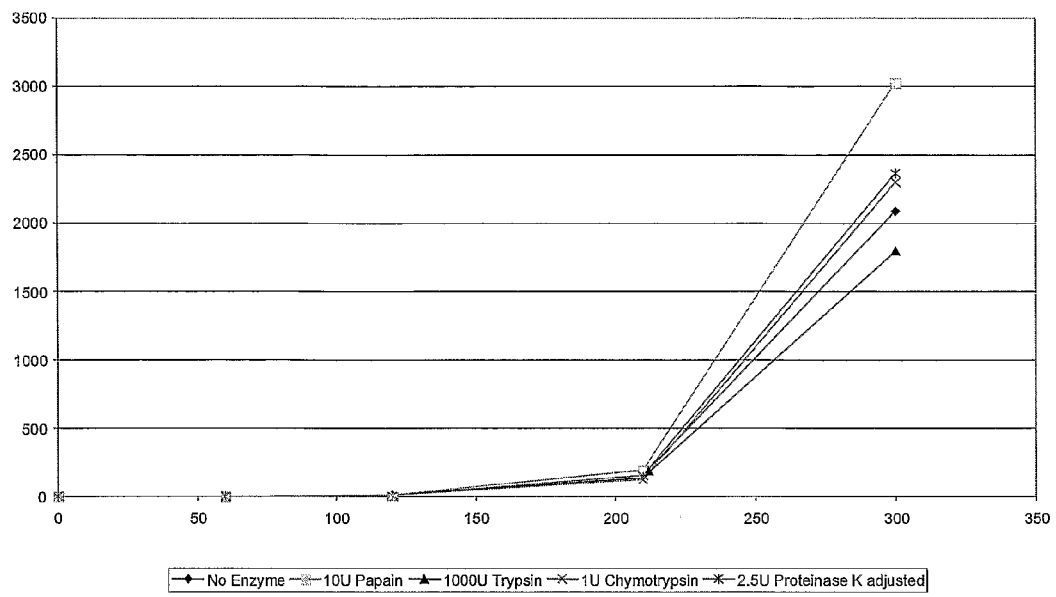
Figure 28:
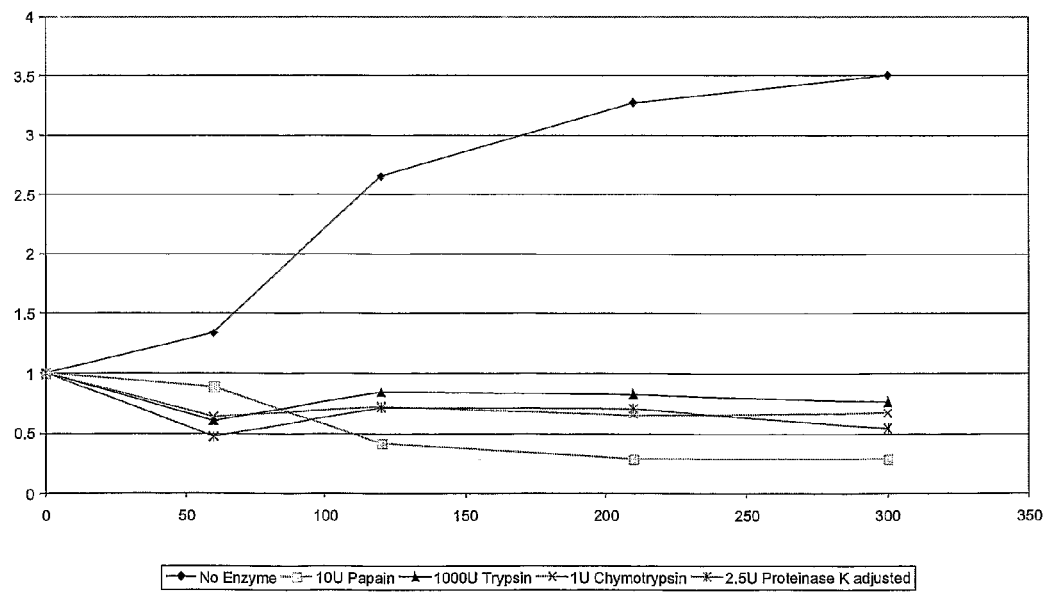
Figure 29:
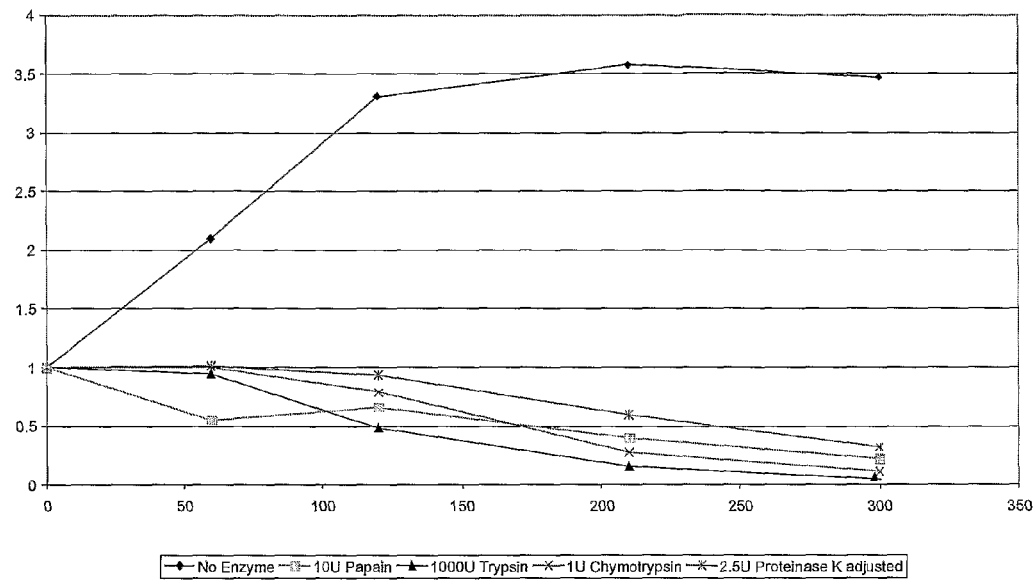
Figure 30:
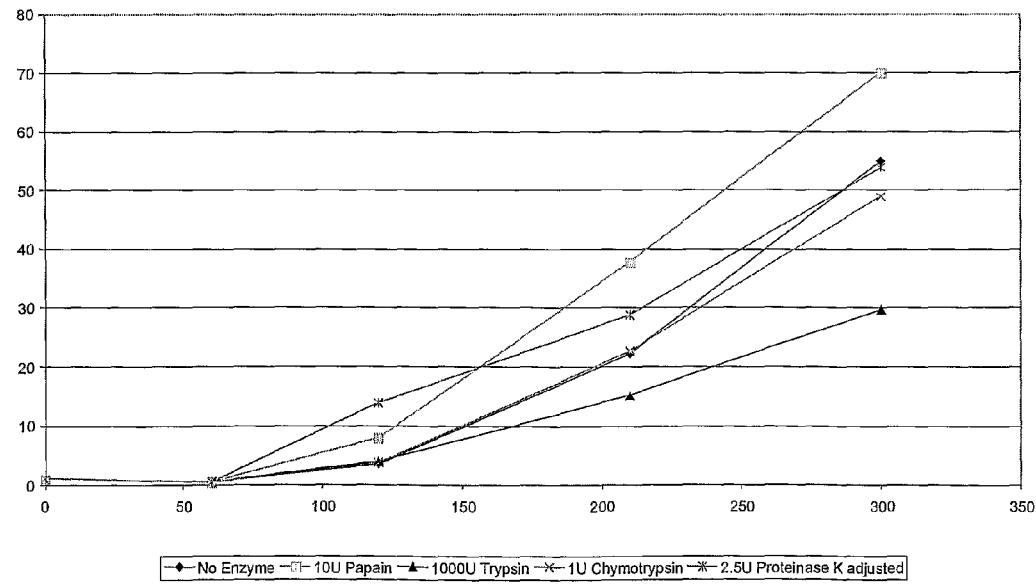

AK was extracted from different organisms and was treated with papain, trypsin, chymotrypsin or proteinase K. Each protease degraded the AK in a similar manner to trypsin. The results are shown in FIG. 19 (*S. epidermis*), 20 (*S. aureus*), 21 (*E. coli*), 22 (*E. faecalis*), 23 (*P. aeruginosa*) and 24 (MRSA). Trypsin is still the protease of choice due to its consistency with both Gram +ve and Gram −ve bacteria.

The Effect of Trypsin on Organisms

To assess whether trypsin affects bacterial growth, $10^3$ cfu/ml organisms were spiked into 1000, 200 and 0 (control) U/ml trypsin/MH samples. These mixtures were incubated at 37° C. for 3 hours, and aliquots were assayed at time 0, 1, 2 and 3 hours. Results are shown in FIGS. 4 to 14.

Thus trypsin at 1000 and 200 U/ml has minimal (if any) effect on the organisms for the 11 species tested. The results for *S. aureus* initially suggest that growth is inhibited by trypsin, but further inspection showed that this was not the case, with the apparent growth inhibition being caused by sampling errors. For all 11 bacteria, therefore, trypsin can be present throughout bacterial incubation without affecting growth Trypsin Digestion of AK in Various Concentrations of Lysed Blood Saponin-lysed blood was serially diluted and mixed with 1000 or 200 U/ml trypsin/MH. The mixtures were incubated at 37° C. for 4 hours, and aliquots assayed at time 0, 1, 2, 3 and 4 hours.

Figure 15:
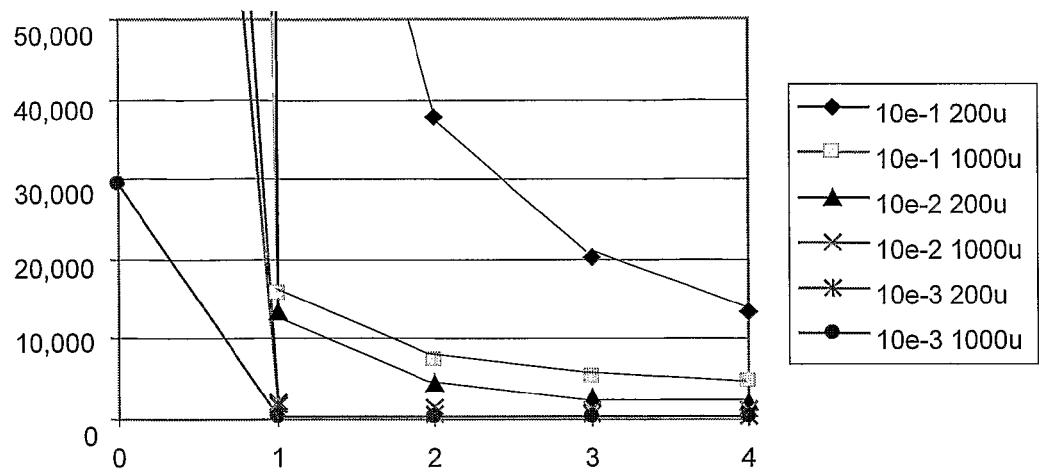
FIG. 15 shows the reduction of blood AK activity caused by trypsin digestion.

Results of the AK assay are shown in FIG. 15.

Using a $10^{-1}$ dilution of blood and 1000 U/ml trypsin, the background was reduced from approximately 100 million to 4,000 RLU in 4 hours, a 25,000 fold reduction. With 1000 U/ml the vast majority of AK digestion appears to occur within the first 2 hours. The reduction in background does then slow and plateau at a certain level, and the plateau seems dependent on the starting background level. This suggests a proportion of the mammalian AK is either inaccessible or unaffected by the trypsin, or that the signal is not AK-related.

Examining Organism Growth Against Lysed Blood Background using Trypsin

Approximately $10^2$ cfu/ml organisms were spiked into a $10^{-1}$ dilution of lysed blood in MH, containing 1000 U/ml trypsin. This was incubated at 37° C. for 4 hours, and aliquots were assayed at time 0, 1, 2, 3 and 4 hours. Results were as follows:

| Organism | | Mean RLU |
|---|---|---|
| Negative | Time 0 | overload |
| | 1 hr | 7,864 |
| | 2 hrs | 3,148 |
| | 3 hrs | 2,001 |
| | 4 hrs | 1,572 |
| *E. coli* | Time 0 | overload |
| | 1 hr | 9,605 |
| | 2 hrs | 7,460 |
| | 3 hrs | 41,121 |
| | 4 hrs | 353,541 |
| *P. aeruginosa* | Time 0 | overload |
| | 1 hr | 8,852 |
| | 2 hrs | 3,582 |
| | 3 hrs | 3,332 |
| | 4 hrs | 8,123 |
| *E. faecalis* | Time 0 | overload |
| | 1 hr | 10,099 |
| | 2 hrs | 4,939 |
| | 3 hrs | 15,587 |
| | 4 hrs | 106,762 |

Based on these results with a starting organism concentration of $10^2$ cfu/ml, using 1000 U/ml trypsin, *E. coli* and *E. faecalis* would be visible against an initial background of around 100 million RLUs within 2 hours, and *P. aeruginosa* would be visible within 4 hours. Thus small numbers of organisms can be detected in blood, despite the high AK background, against a high background in $\leq 4$ hours.

Examining Trypsin Treatment of Platelets

To a 0.5 mL test sample of contaminated platelets, 40 µL of a 5% Triton X-100 solution and 150 µl of P-Per was added and then incubated for 10 minutes with gentle shaking at ambient temperature. The mix was then centrifuged at 13000 rpm for 3.5 minutes.

The supernatant was then removed and the pellet was resuspended in 1.5 ml of sterile water by repeated pipetting. The mix was then centrifuged at 13000 rpm for 3.5 minutes.

The supernatant was then removed and the pellet was resuspended in 0.5 ml of LB broth containing 1000 U/ml trypsin and incubated for 20 mins at 37° C.

The AK activity was then assayed as described above at intervals up to 4 hours.

The results (FIGS. 17 and 18) show that the assay can be used to detect contamination of platelets at levels as low as $10^2$-$10^3$ organisms/ml.

Effect of Proteases on Whole Bacterial Organisms in Antibiotics

An assay was carried out (as described below) to see what effect the presence of protease had on the activity of antibiotics.

Recovery and Testing of Bacterial Adenylate Kinase
1. Bacteria scrapped from a plate were inoculated in 1 ml of broth only and incubated at 37° C. for 1 hour.
2. Antibiotic broth was prepared by adding the 3 antibiotic tabs (collistin, ciprofloxacin and oxacillin) to 200 ml of broth only.
3. The target (e.g. MRSA) or resistant (e.g. *S. epidermidis*) bacterial strains were diluted to approximately $10^5$ cpm/ml, while non target or sensitive bacterial strains were diluted to approximately $10^6$ cpm/ml.

4. Enzyme stocks were set up (as described above) in Antibiotic broth.
5. 1.98 ml solutions set up as below and incubated at 37° C. for 1 hour.

|  | No enzyme control | 10 U/ml Papain | 2.5 U/ml Proteinase K | 1.0 U/ml Chymotrypsin | 1000 U/ml Trypsin |
|---|---|---|---|---|---|
| Broth with antibiotics (ml) | 1.98 | 1.78 | 1.78 | 1.78 | 1.78 |
| 10x Enzyme stocks (ml) | 0 | 0.2 | 0.2 | 0.2 | 0.2 |

6. The bacterial dilution (from step 3) was then diluted 100 fold and assayed for adenylate kinase activity in triplicate and averaged. This was used as the time point zero average.
7. 20 µl of the appropriate bacterial dilution (from step 3) was then added to the solutions (from step 5) and incubated at 37° C.
8. Samples were assayed for adenylate kinase at set time points in triplicate.
9. Triplicates averaged and normalised by division against the time point zero average.

The results (see FIGS. 25-30) demonstrate that the antibiotics are unaffected by the proteases and still kill and lyse, partially or fully depending on the antibiotic and target bacteria, the unwanted non-target bacteria. In particular, the samples with the enzymes generally give lower RLU's compared to the controls, as the AK that is released is degraded. This is more noticeable with the Gram negative bacteria (*E. coli* and *P. aeruginosa*) due to the proteases being highly effective at knocking out their AK. *S. epidermidis* also appears quite affected by the enzymes. *E. faecalis* growth is slow but appears to be unaffected by the enzymes. It is resistant, hence the growth, and doesn't lyse enough for the enzymes to get to the AK and lower the RLU. More importantly, the MRSA growth appears to be unaffected by the enzymes and antibiotics. Thus, the results show that the proteases do not interfere with the antibiotics. It will be understood that the invention has been described by way of example only and modifications may be made whilst remaining within the scope and spirit of the invention.

REFERENCES

The Contents of Which are Hereby Incorporated by Reference

[1] http://www.altcorp.com/AffinityLaboratory/introgcf.htm
[2] WO94/17202.
[3] WO96/02665.
[4] Squirrell et al. (1994) *Adenylate kinase as a cell marker in bioluminescent assays*. In: Campbell A K, Kicka L J, Stanley P E (editors). *Bioluminescence and Chemiluminescence: Fundamentals and Applied Aspects*. Chichester: John Wiley and Sons, pages 486-9.
[5] Sanders (1994) *A rapid bioluminescent technique for the detection and identification of Listeria monocytogenes in the presence of Listeria innocua*. Pages 454-7 of same volume as for ref. 4.
[6] WO00/70082.
[7] Blasco et al. (1998) *Journal of Applied Microbiology* 84:661ff.
[8] WO00/46357.
[9] WO99/23489.
[10] Bean et al. (1992) *International Journal of Cell Cloning* 10:190-5.
[11] Konstantinova (1972) *Dokl Akad Nauk SSSR* 203:1204-6.
[12] Perrier et al. (1998) *J Biol Chem* 273:19097-101.
[13] Fraser et al. (1997) *Biochem J* 323:711-8.
[14] Balows (1974) *Current techniques for antibiotic susceptibility testing*. ISBN: 0398028869.
[15] Smaill (2000) *Can J Gastroenterol* 14:871-875.
[16] Baquero (1990) *Eur J Clin Microbiol Infect Dis* 9:492-495.
[17] Baselski (1996) *Clin Lab Med*. 16:49-60.
[18] Kassimi et al. (2002) *J Virol Methods* 101:197-206.
[19] Zhang & Weintraub (1998) *J Clin Microbiol* 36:3545-3548.
[20] Dowd et al. (1998) *Appl Environ Microbiol* 64:333-336.
[21] Li et al (1996) *J Clin Microbiol* 34:1903-1907.
[22] Shetab et al. (1998) *J Clin Microbiol* 36:1729-1732.
[23] Homes et al. (1991) *J Clin Microbiol* 29:2375-2379.

The invention claimed is:

1. A method for detecting the absence or presence of cells of interest in a liquid sample, the method comprising:
providing a sample comprising an extracellular medium containing an enzyme with adenylate kinase activity and suspected of further comprising cells of interest that comprise an intracellular enzyme having adenylate kinase activity;
treating the sample with a reagent that inactivates adenylate kinase activity in the extracellular medium, wherein the reagent is selected from the group consisting of an acid, a base, and a proteolytic enzyme;
lysing the cells of interest, thereby releasing the intracellular enzyme having adenylate kinase activity; and
measuring adenylate kinase activity of the released intracellular enzyme.

2. The method of claim 1, wherein the cells of interest are microorganism cells.

3. The method of claim 2, wherein the microorganism cells comprise bacterial cells.

4. The method of claim 1, wherein the sample comprises a blood sample.

5. The method of claim 4, wherein the blood sample comprises blood cells that have been lysed and unlysed microbial cells.

6. The method of claim 1, wherein the adenylate kinase activity comprises ATP production.

7. The method of claim 1, wherein the reagent comprises a protease.

8. The method of claim 7, wherein the protease comprises trypsin.

9. The method of claim 6, wherein the ATP production is measured using a luciferase/luciferin reaction.

10. A method comprising:
  providing a sample comprising an extracellular medium containing an enzyme having adenylate kinase activity and suspected of further comprising cells of interest containing an intracellular enzyme having adenylate kinase activity;
  treating the sample with a reagent that inactivates adenylate kinase activity in the extracellular medium but does not inactivate adenylate kinase activity in the cells of interest, wherein the reagent is selected from the group consisting of an acid, a base, and a proteolytic enzyme;
  establishing a culture of the cells of interest remaining after the sample is treated to inactivate the extracellular adenylate kinase activity;
  removing one or more subsamples from the culture of cells of interest;
  lysing cells of interest in the subsample to release the intracellular enzyme; and
  measuring adenylate kinase activity of the released intracellular enzyme.

11. The method of claim 10 further comprising repeating the steps of removing one or more subsamples, lysing cells of interest, and measuring the adenylate kinase activity at different times; and
  comparing the adenylate kinase activity measured at the different times.

12. A method for detecting the absence or presence of cells of interest in a liquid sample, the method comprising:
  providing a sample comprising an extracellular medium containing an enzyme with a measurable enzymatic activity and suspected of further comprising cells of interest that comprise an intracellular enzyme having the measurable enzymatic activity;
  treating the sample with a reagent that inactivates the measurable enzymatic activity in the extracellular medium, wherein the reagent comprises a protease;
  lysing the cells of interest, thereby releasing the intracellular enzyme having the measurable enzymatic activity; and
  measuring the measurable enzymatic activity of the released intracellular enzyme, wherein the measurable enzymatic activity comprises adenylate kinase activity.

13. A method for detecting the absence or presence of cells of interest in a liquid sample, the method comprising:
  providing a sample comprising blood cells or serum, the sample suspected of further comprising cells of interest that comprise an intracellular adenylate kinase enzymatic activity;
  treating the sample with trypsin;
  lysing the cells of interest, thereby releasing the intracellular adenylate kinase enzymatic activity; and
  measuring the released intracellular adenylate kinase enzymatic activity.

* * * * *

UNITED STATES PATENT AND TRADEMARK OFFICE
CERTIFICATE OF CORRECTION

| | |
|---|---|
| PATENT NO. | : 8,349,583 B2 |
| APPLICATION NO. | : 11/919832 |
| DATED | : January 8, 2013 |
| INVENTOR(S) | : Marc Green et al. |

It is certified that error appears in the above-identified patent and that said Letters Patent is hereby corrected as shown below:

Column 4,
Line 22, "*Koxytoca)*," should read --*K. oxytoca)*,--.
Line 31, "*Boidetella*" should read --*Bordetella*--.

Column 11,
Line 62, "*narcescens.*" should read --*marcescens.*--.

Column 13,
Line 40, "(MH$^+$)" should read --(MH)--.
Line 45, the heading for the second column in the table should read --Trypsin Concentration--.

Column 15,
Line 22, "100" should read --100µl--.

Column 16,
Line 10, the heading for the second column in the table should read --Incubation period--.

Column 17,
Line 67, "84.661ff" should read --84.661 ff.--.

Column 18,
Line 30, "et al" should read --et al.--.

Signed and Sealed this
Second Day of April, 2013

Teresa Stanek Rea
*Acting Director of the United States Patent and Trademark Office*